United States Patent [19]
Wood et al.

[11] Patent Number: 6,114,549
[45] Date of Patent: Sep. 5, 2000

[54] PROCESS OF MAKING 3-PHENYL-1-METHYLENEDIOXYPHENYL-INDANE-2-CARBOXYLIC ACID DERIVATIVES

[75] Inventors: Jeffery L. Wood, Blue Bell; Michael Anthnoy McGuire, West Norriton; Robert John Mills, Norristown; Lendon Norwood Pridgen, Collegeville; Marvin Sungwhan Yu, Audubon; Qiaogong Su, Norristown, all of Pa.

[73] Assignee: SmithKline Beecham Corporation, Philadelphia, Pa.

[21] Appl. No.: 08/776,803

[22] PCT Filed: Nov. 8, 1996

[86] PCT No.: PCT/US96/18082

§ 371 Date: May 8, 1998

§ 102(e) Date: May 8, 1998

[87] PCT Pub. No.: WO97/17330

PCT Pub. Date: May 15, 1997

Related U.S. Application Data

[60] Provisional application No. 60/006,330, Nov. 8, 1995.

[51] Int. Cl.$^7$ ................................................. C07D 317/70
[52] U.S. Cl. ........................ 549/432; 546/112; 546/183; 546/281.7
[58] Field of Search .................... 546/112, 183, 546/279, 281.7; 549/432

[56] References Cited

U.S. PATENT DOCUMENTS 5,389,620  2/1995  Ishikawa et al. .................... 514/80

FOREIGN PATENT DOCUMENTS

| 325 571 A1 | 7/1989 | European Pat. Off. . |
| WO 93/08799 | 5/1993 | WIPO . |
| WO 94/24119 | 10/1994 | WIPO . |
| WO 94/25013 | 11/1994 | WIPO . |

OTHER PUBLICATIONS

Database CAPLUS on STN, Chemical Abstract No. 120:106563 (SmithKline Beecham Corporation), abstract, compounds with Registry No. 150355–66–1, 150355–80–9, 150355–81–0, 150355–82–1, 150355–83–2, 150355–86–5, 150355–87–6, 150355–69–7, 150356–70–0, 150731–08–1, 150824–40–1, 150356–65–3, and 150356–66–4, Feb. 1994.

Database CAPLUS on STN, Chemical Abstract No. 123:169596 (SmithKline Beecham Corporation), abstract, compounds with Registry No. 167255–97–2, 167255–98–3, 167255–99–4, 167256–00–0, 167256–03–0, 156129–15–6, 167084–49–3, 167256–05–5, 150731–08–1, 157659–79–5, 167084–72–2, 167084–76–6, and 167256–08–8, Sep. 1995.

Database CAPLUS on STN, Chemical Abstract No. 122:213929, (Morinaga Milk Industry Co., Ltd.), abstract and a compound with Registry No. 842–01–3, Apr. 1995.

Database CAPLUS on STN, Chemical Abstract No. 120:334982, (Japan Synthetic Rubber Co. Ltd.), abstract and compounds with Registry No. 155377–86–9 and 113400–27–4, Jun. 1994.

Database CAPLUS on STN, Chemical Abstract No. 112:55211, (Babivitrum AB), abstract, compounds with Registry No. 33921–65–2, 57322–71–1, 103849–16–7, 124938–04–1, 40545–949, 51737–00–9, 73108–72–2, and 88407–29–8, Feb. 1990.

Database CAPLUS on STN, Chemical Abstract No. 78:97557, (Naumov, Y.A. et al.), abstract and compounds with Registry No. 40424–16–6 and 40424–20–2, Apr. 1973.

Database CAPLUS on STN, Chemical Abstract No. 112:178878 (Ma, Z. et al.), abstract and a compound with Registry No. 126280–78–2, May 1990.

Database CAPLUS on STN, Chemical Abstract No. 116:106292, (British Petroleum Co., PLC, abstract and a compound with Registry No. 139237–81–3, Mar. 1992.

Database CAPLUS on STN, Chemical Abstract No. 116;174316, (Melnyk, O. et al.), abstract and compounds with Registry No. 113675–83–5 and 139962–45–1, Apr. 1992.

*Primary Examiner*—Amelia Owens
*Attorney, Agent, or Firm*—Wayne J. Dustman; William T. King; Charles M. Kinzig

[57] ABSTRACT

Invented is an improved process for preparing aromatic ring-fused cyclopentane derivatives. Preferred compounds prepared by this invention are indane carboxylates and cyclopentano[b]pyridine derivatives. The most preferred compounds prepared by this invention are (+)(1S, 2R, 3S)-3-[2-(2-hydroxyeth-1-yloxy)4-methoxyphenyl]-1-(3,4-methylenedioxyphenyl)-5-(prop-1-yloxy)indane-2-carboxylic acid and pharmaceutically acceptable salts thereof and (+)(1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Also invented are novel intermediates useful in preparing these compounds.

30 Claims, No Drawings

PROCESS OF MAKING 3-PHENYL-1-METHYLENEDIOXYPHENYL-INDANE-2-CARBOXYLIC ACID DERIVATIVES

This application claims benefit of Provisional Application No. 60/006,330 filed Nov. 8, 1995.

FIELD OF THE INVENTION

The present invention relates to an improved process for preparing aromatic ring-fused cyclopentane derivatives. Preferably, the present invention relates to an improved process for preparing indane carboxylates and cyclopentano[b]pyridine derivatives. Advantageously, the present invention relates to an improved process for preparing (+) (1S, 2R, 3S)-3-[2-(2-hydroxyeth-1-yloxy)4-methoxyphenyl]-1-(3,4-methylenedioxyphenyl)-5-(prop-1-yloxy)indane-2-carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof. Such compounds are described in International Application Number: PCT/US94/04603-International Publication Number WO 94/25013 published on Nov. 10, 1994 and in U.S. Pat. No. 5,389,620, as being useful as endothelin receptor antagonists. Also invented are novel intermediates useful in preparing these compounds.

BACKGROUND OF THE INVENTION

Processes for the preparation of indane carboxylates, specifically (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2-carboxylic acid have previously been described. In particular a multistep process to prepare (+) (1S, 2R, 3S)-3-(2-carboxymethoxy-4-methoxyphenyl)-1-(3,4-methylenedioxyphenyl)-5-(prop-1-yloxy)indane-2-carboxylic acid in 6% overall yield (not including a racemic separation step) from methyl 3-(prop-1-yloxy)benzoylacetate and a multistep process to prepare (+) (1S, 2R, 3S)-3-[2-(2-hydroxyeth-1-yloxy)4-methoxyphenyl]-1-(3,4-methylenedioxyphenyl)-5-(prop-1-yloxy)indane-2-carboxylic acid in 2% overall yield (not including a racemic separation step) from methyl 3-(prop-1-yloxy)benzoylacetate is reported in International Publication Number WO 94/25013, published Nov. 10, 1994. The syntheses of these molecules are complicated by the presence of three chiral centers in each compound.

Processes for the preparation of cyclopentano[b]pyridine derivatives have previously been described. In particular, multistep processes to prepare cyclopentano[b]pyridine derivatives, in low over all yield, are reported in U.S. Pat. No. 5,389,620.

Thus, there is a need in the art for an economical method to prepare indane carboxylates and cyclopentano[b]pyridine derivatives, specifically (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof and (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof.

The numerous advantages of the presently invented process and intermediates will become apparent upon review of the following description.

SUMMARY OF THE INVENTION

This invention relates to an improved process for preparing aromatic ring-fused cyclopentane derivatives.

This invention also relates to novel intermediates useful in preparing aromatic ring-fused cyclopentane derivatives.

This invention relates to an improved process for preparing indane carboxylates.

This invention also relates to novel intermediates useful in preparing indane carboxylates.

This invention relates to an improved process for preparing cyclopentano[b]pyridine derivatives.

This invention also relates to novel intermediates useful in preparing cyclopentano[b]pyridine derivatives.

This invention relates to an improved process for preparing (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and pharmaceutically acceptable salts thereof, preferably the ethylene diamine 2:1 salt.

This invention relates to novel intermediates useful in preparing (+) (1S, 2R, 3S)-3-[2-(2-hydroxyeth-1-yloxy)4-methoxyphenyl]-1-(3,4-methylenedioxyphenyl)-5-(prop-1-yloxy)indane-2-carboxylic acid.

This invention relates to an improved process for preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid and pharmaceutically acceptable salts thereof, preferably the disodium salt.

This invention relates to novel intermediates useful in preparing (+) (1S, 2R, 3S)-3-(2-carboxymethoxy-4-methoxyphenyl)-1-(3,4-methylenedioxyphenyl)-5-(prop-1-yloxy)indane-2-carboxylic acid.

DETAILED DESCRIPTION OF THE INVENTION

Unless otherwise defined, the term 'aromatic ring-fused cyclopentane derivatives' as used herein, is meant to refer to the racemic compounds of Formula (1):

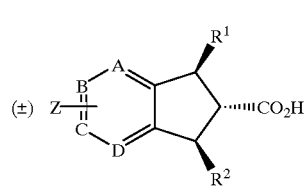

(1)

wherein A, B, C and D are carbon atoms or three of A, B, C and D are carbon atoms and one is a nitrogen atom;

$R^1$ is

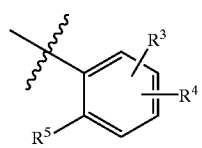

where $R^3$ and $R^4$ are independently H, OH, protected OH, $C_{1-8}$alkoxy, Br, F, I, Cl, $CF_3$ or $C_{1-6}$alkyl and $R^5$ is —$OCH_2CO_2H$ or —$OCH_2CH_2OH$;

$R^2$ is

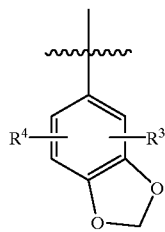

where $R^3$ and $R^4$ are as indicated above and
Z is H, OH, or $C_{1-5}$alkoxy;
or a pharmaceutically acceptable salt thereof.

Preferred among the racemic compounds of Formula (1) are the compounds of Formula (17):

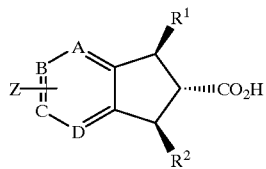

(17)

wherein A, B, C, D, $R^1$, $R^2$ and Z are as described in Formula (1);
or a pharmaceutically acceptable salt thereof By the term indane carboxylates as used herein is meant the racemic compounds of Formula (2):

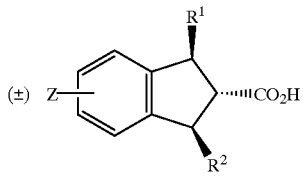

(2)

wherein $R^1$, $R^2$ and Z are as described in Formula (1);
or a pharmaceutically acceptable salt thereof.

Preferred among the racemic compounds of Formula (2) are the compounds of Formula (18):

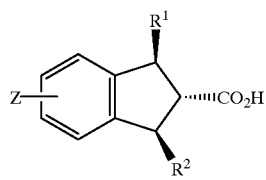

(18)

wherein $R^1$, $R^2$ and Z are as described in Formula (1);
or a pharmaceutically acceptable salt thereof.

By the term cyclopenteno[b]pyridine derivatives as used herein is meant the racemic compounds of Formula (3):

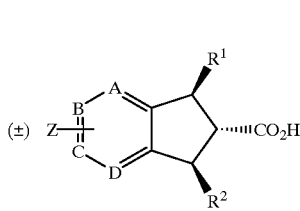

(3)

wherein three of A, B, C and D are carbon atoms and one is a nitrogen atom; and $R^1$, $R^2$ and Z are as described in Formula (1);
or a pharmaceutically acceptable salt thereof.

Preferred among the racemic compounds of Formula (3) are the compounds of Formula (19):

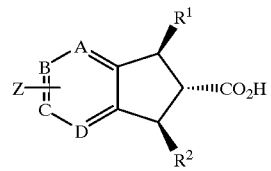

(19)

wherein three of A, B, C and D are carbon atoms and one is a nitrogen atom; and $R^1$, $R^2$ and Z are as described in Formula (1);
or a pharmaceutically acceptable salt thereof.

In Formula (3) compounds, in Formula (19) compounds and in Formula (1) compounds when one of A, B, C or D is a nitrogen atom, preferably A is nitrogen.

Pharmaceutically acceptable salts of the compounds of Formulas (1), (2), (3), (17), (18) and (19) are formed where appropriate by methods well known to those of skill in the art.

Pharmaceutically acceptable salts of (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid and (+) (1S, 2R, 3S)-3-(2-carboxymethoxy-4-methoxyphenyl)-1-(3,4-methylenedioxyphenyl)-5-(prop-1-yloxy)indane-2-carboxylic acid are formed where appropriate by methods well known to those of skill in the art.

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid as used herein utilizes standard chemical terminology and refers to a compound of the structure

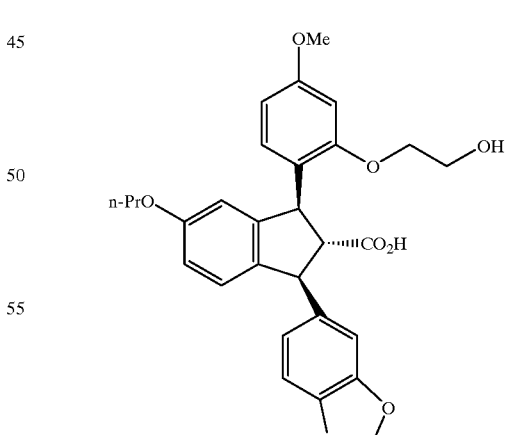

(X)

The term (+) (1S, 2R, 3S)-3-[2-(2-hydroxyeth-1-yloxy)-4-methoxyphenyl]-1-(3,4-methylenedioxyphenyl)-5-(prop-1-yloxy)indane-2-carboxylic acid ethylene diamine salt (2:1) as used herein utilizes standard chemical terminology and refers to Compound (i)

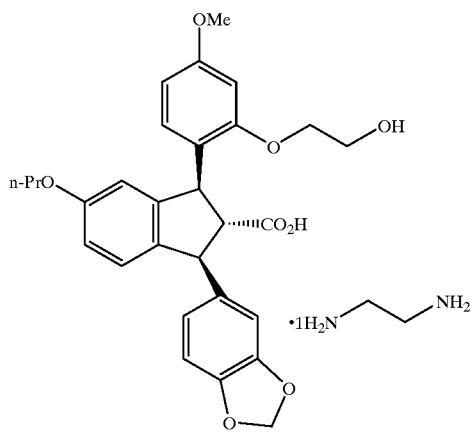

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid as used herein utilizes standard chemical terminology and refers to a compound of the structure (Y)

(Y)

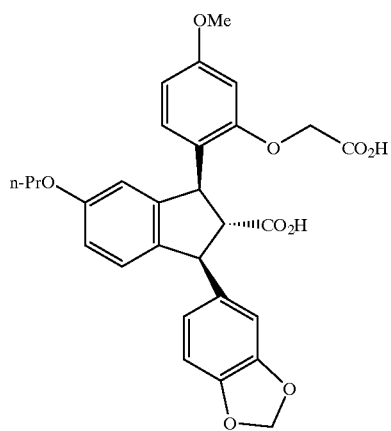

The term (+) (1S, 2R, 3S)-3-(2-carboxymethoxy-4-methoxyphenyl)-1-(3,4-methylenedioxyphenyl)-5-(prop-1-yloxy)indane-2-carboxylic acid disodium salt as used herein utilizes standard chemical terminology and refers to Compound (g)

(g)

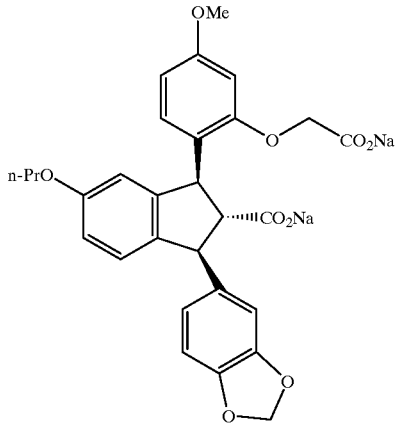

The indane carboxylates of Formula (18) of the current invention are prepared by methods outlined in the Schemes below and in the Examples from compounds of Formula (4):

(4)

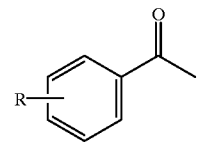

where R is H, OH, $C_{1-5}$alkoxy (preferably n-PrO) or a protected oxy group, such as benzyloxy. Compounds of Formula (4) are known or can be prepared from readily available starting materials by those skilled in the art.

The compounds of Formula (4) can be converted into the compounds of Formula (a)

(a)

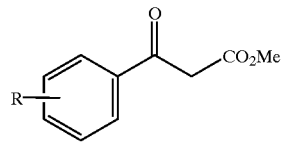

where R is as described above, by known methods such as those described in International Publication Number WO 94/25013, published Nov. 10, 1994 in Example 1, section b) on page 20.

By the term 'protected oxy group' and 'protected OH' as used herein, is meant any conventional blocking group in the art such as described in "Protective Groups in Organic Synthesis" by Theodora W. Greene, Wiley-Interscience, 1981, New York, provided that such protected oxy groups or such protected OH do not include moieties that render inoperative the presently invented process. A preferred protected oxy group for use herein is benzyloxy. A preferred protected OH for use herein is benzyloxy.

Further, when necessary or desired, R can be converted to a substituent of Z. Reactions to convert R to Z are performed on products of the synthetic pathways disclosed or claimed herein or, where appropriate or preferable on certain intermediates in these synthetic pathways. For example, hydroxyl groups can be converted into $C_{1-5}$alkoxy groups by alkylation. Protected oxy groups can be deprotected and further reacted to form a substituent of Z.

The present invention provides an improved process for the production of indane carboxylates of Formula (18) as indicated in Schemes 1 to 3 below.

Scheme 1

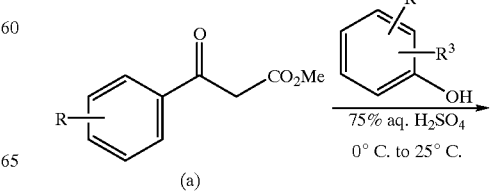

(a)

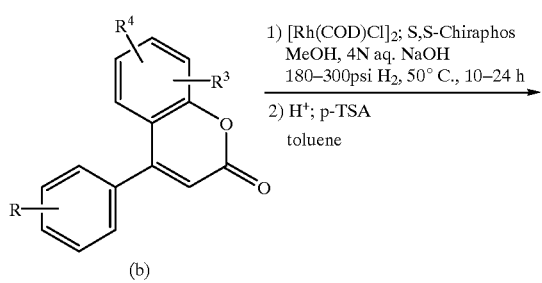

(b)

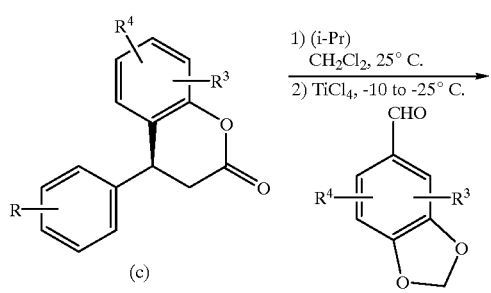

(c)

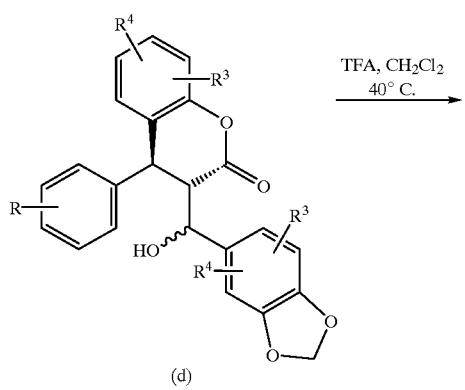

(d)

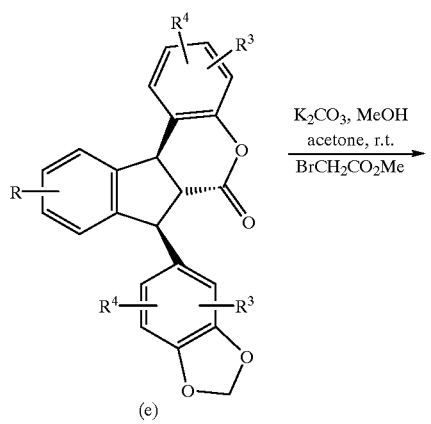

(e)

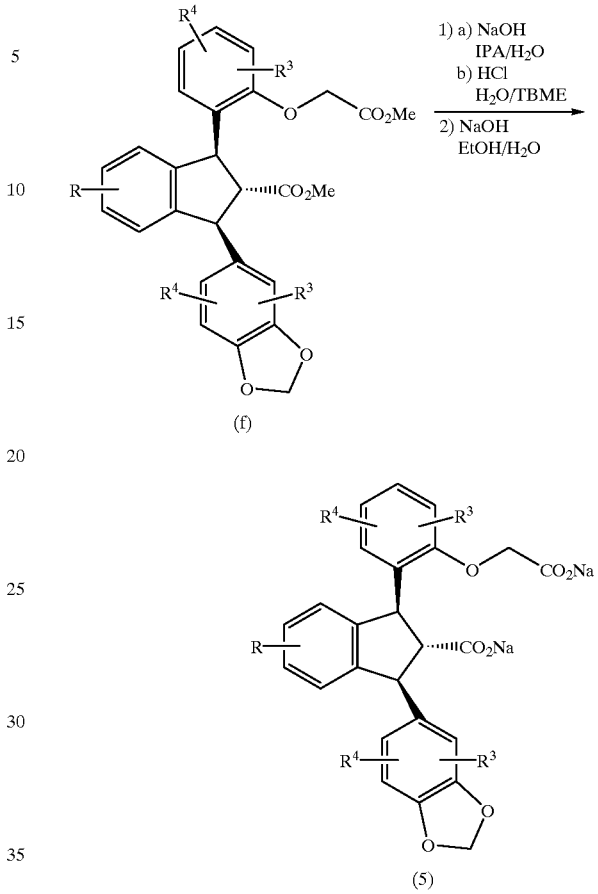

(f)

(5)

Scheme 1 outlines formation of indane carboxylates wherein $R^5$ is —$OCH_2CO_2H$, preferably the disodium salt, Compound (g). As used in Scheme 1, $R^3$ and $R^4$ are as described in Formula (1) and R is as described in Formula (4). Compounds of Formula (b) are prepared by treating compounds of Formula (a) with a phenol under acidic conditions. Compounds of Formula (c), as the predominately pure enantiomer, are prepared by catalytic hydrogenation of Formula (b) compounds using a chiral catalyst such as [(S)-(−)-2,2'-Bis(diphenylphosphino)-1,1'-binaphthyl]chloro(p-cymene)ruthenium chloride (as used herein, Ru-(S)-(−)-BINAP) at approx. 1–5 atm $H_2$, (Bicyclo [2.2.1]hepta-2,5-diene)[2S, 3S]-bis(diphenylphosphino) butane]-rhodium(I) perchlorate (as used herein, Rh-(S,S)(Chiraphos)(NBD)$ClO_4$) at approx. 400 psi $H_2$ or preferably, the catalyst prepared by combining [Rh(COD)$Cl_2$ with S,S-Chiraphos, at approx. 180–300 psi. Compounds of Formula (d), as used herein Formula (d) compounds refer to the indicated alcohol diastereomers, are prepared by combining Formula (c) compounds with the indicated piperonal in an aldol reaction, most preferably by using titanium (IV) chloride in the presence of a base, preferably a hindered amine base, such as N, N-diisopropylethylamine. Formula (d) compounds are treated with an acid to cause Friedel-Crafts alkylation to give the predominately pure enantiomer as Formula (e) compounds. Treatment of Formula (e) compounds with base in the presence of methanol and methyl bromoacetate gives the diester as Formula (f) compounds. Saponification of Formula (f) compounds affords the diacid (preferably Compound Y as used herein) which is treated with sodium hydroxide to give Formula (5) compounds (preferably Compound (g) as used herein)

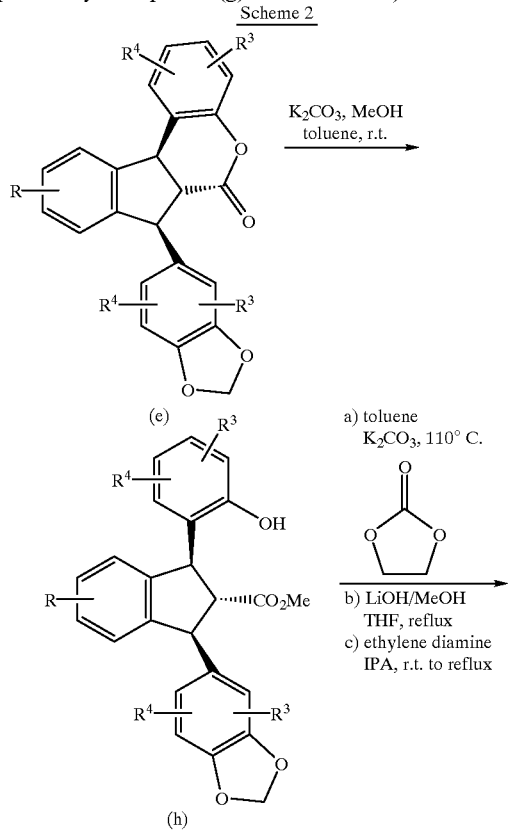

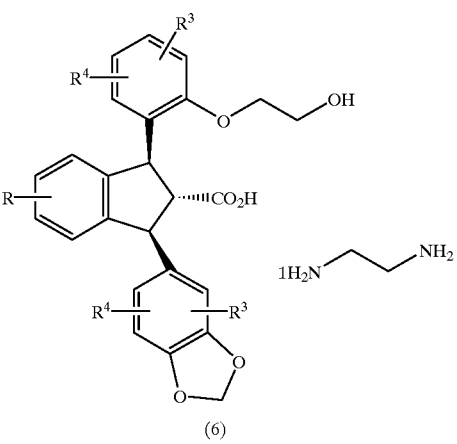

Scheme 2 outlines formation of indane carboxylates wherein $R^5$ is —$OCH_2CH_2OH$, preferably the ethylene diamine salt (2:1) of Compound (i). As used in Scheme 2, $R^3$ and $R^4$ are as described in Formula (1) and R is as described in Formula (4). Formula (e) compounds from Scheme 1 are treated with base in the presence of methanol to give the phenol-ester Formula (h) compounds. Alkylation of Formula (h) compounds followed by saponification with lithium hydroxide monohydrate affords the acid (preferably Compound (X) as used herein), which is treated with ethylene diamine to give Formula (6) compounds.

In an alternative aspect of the invention novel intermediates of Formula (c) and Formula (d) are prepared according to Scheme 3 below.

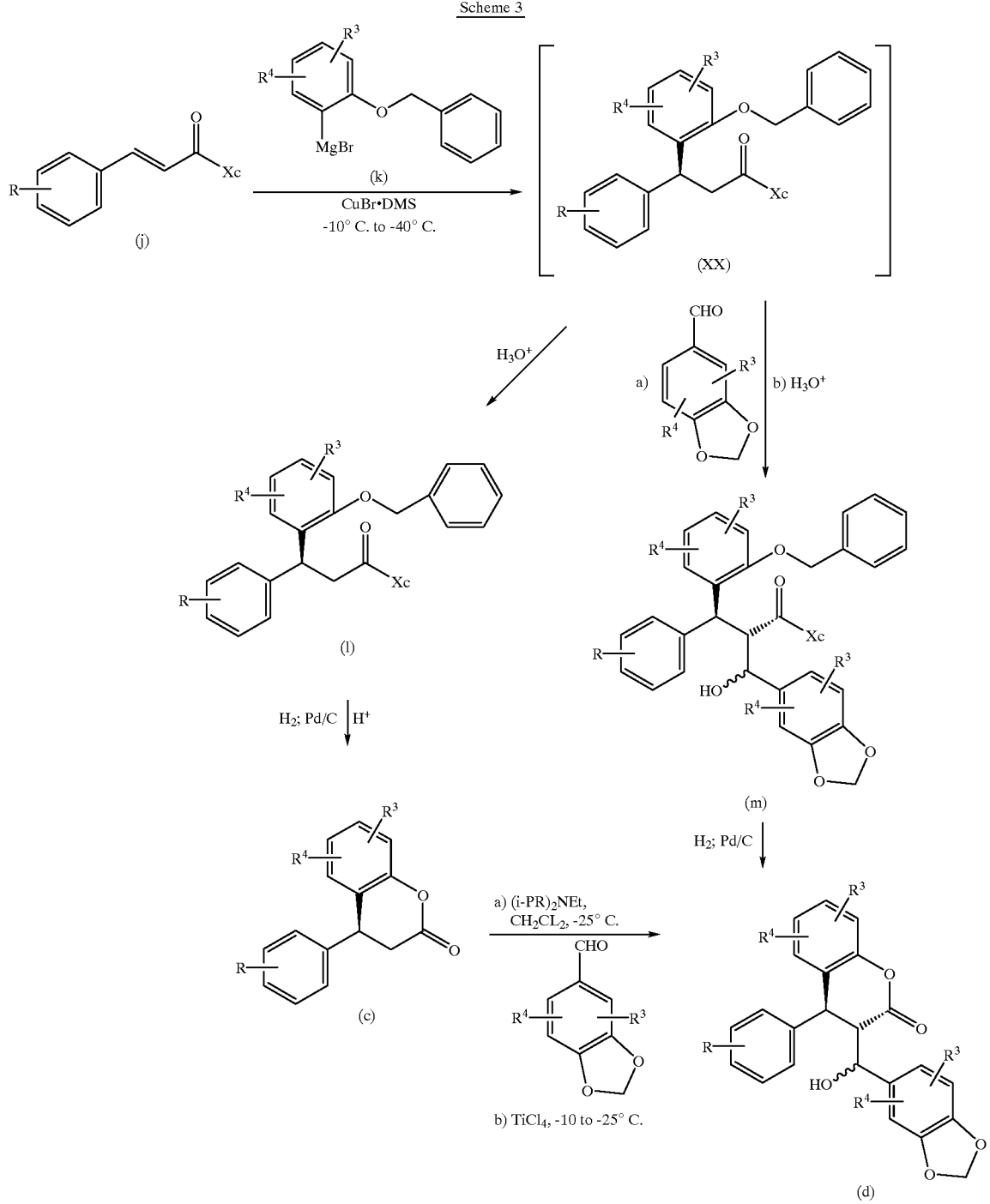

Scheme 3 outlines a process for the formation of compounds of Formula (c) and compounds of Formula (d). As used in Scheme 3, $R^3$ and $R^4$ are as described in Formula (1), provided that $R^3$ and $R^4$ are not Br, I or Cl, and R is as described in Formula (4). Compounds of Formula (j) can be prepared by treating a compound of the formula $HX_c$, where $HX_c$, is as described below, with lithium bis(trimethylsilyl) amide with the subsequent addition of an appropriately substituted (E)-3-phenyl-2-propenoyl chloride compound. Compounds of Formula (I) are prepared by treating cuprous bromide-dimethyl sulphide complex in dimethylsulphide/ THF with an appropriate 1-magnesiumbromide-2-benzyloxybenzene compound, followed by the addition of a compound of Formula (j). The Formula (l) compound is treated with palladium on carbon in a hydrogen atmosphere to give a compound of Formula (c).

As used in Scheme 3 compounds of Formula (m) are prepared by treating cuprous bromide-dimethyl sulphide complex in dimethylsulphide/THF with an appropriate 1-magnesiumbromide-2-benzyloxybenzene compound, followed by the addition of a compound of Formula (j), followed by the addition of piperonal. Formula (m) compounds are treated with palladium on carbon in a hydrogen atmosphere to give Formula (d) compounds.

As used in the specification and in the claims the term $X_c$ means a chiral auxiliary. By the term "chiral auxiliary" as used in the specification and in the claims is meant a non-racemic functional group that imparts a diastereoselective reaction at a remote prochiral center of a molecule. Chiral auxiliaries as used herein are formed by reaction with a compound of the formula $HX_c$, wherein $X_c$ is as described above. Examples of $HX_c$, as used herein include: 8-phenylmenthol (such as described in D. Comins et al. *J. Org. Chem.* vol. 58, 4656 (1993)), N-substituted borane-2, 10-sultams (such as described in W. Oppolzer *J. Am. Chem. Soc.*, 112 2767 (1990)), preferably, 4-substituted or 4,5-substituted 2-oxazolidinones derived from amino acid derivatives such as phenylglycinol or valinol (such as described in D. Evans et al. *J. Am. Chem. Soc.*, 109, 6881 (1987) and in D. Evans et al. *Tet. Lett.*, 28, 1123 (1990)) and, most preferably, 4-substituted or 4,5-substituted 2-imidazolidinones derived from compounds such as ephedrine (such as described in S. E. Drewes, et al. *Chem. Ber.*, 126, 2663 (1993)).

The racemic compounds of Formulas (1), (2) and (3) are prepared according to the methods outlined in Schemes (1) and (2) and in the Examples by substituting a compound of Formula (7):

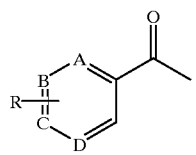

(7)

wherein A, B, C and D are carbon atoms or three of A, B, C and D are carbon atoms and one is a nitrogen atom and R is H, OH, $C_{1-5}$alkoxy (preferably n-PrO) or a protected oxy group, such as benzyloxy, for the compound of formula (4) and by substituting the corresponding achiral catalyst for the chiral catalyst disclosed in Scheme 1 for the preparation of Formula (c) compounds.

Compounds of Formula (7) are known or can be prepared from readily available starting materials by those skilled in the art.

The compounds of Formula (7) can be converted into the compounds of Formula (8)

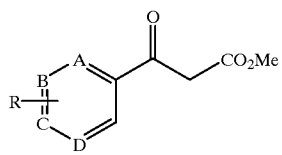

(8)

where A, B, C, D and R are as described in Formula (7), by known methods such as those described in International Publication Number WO 94/25013, published Nov. 10, 1994 in Example 1, section b) on page 20.

Thus, the compounds of Formula (8) are utilized in Schemes 1 and 2, using an achiral catalyst in the Formula (b) to Formula (c) transformation, to prepare compounds of Formula (1) and intermediates useful in preparing compounds of formula (1). The compounds of Formula (a) are utilized in Schemes 1 and 2, by substituting an achiral catalyst in the Formula (b) to Formula (c) transformation, to prepare compounds of Formula (2) and intermediates useful in preparing compounds of formula (2). The compounds of Formula (8), wherein three of A, B, C and D are carbon atoms and one is a nitrogen atom, are utilized in Schemes 1 and 2, using an achiral catalyst in the Formula (b) to Formula (c) transformation, to prepare compounds of Formula (3) and intermediates useful in preparing compounds of formula (3).

The cyclopenteno[b]pyridine derivatives of Formula (19) of the current invention are prepared according the methods outlined in Schemes 1 to 3 and in the Examples from compounds of Formula (8) wherein three of A, B, C and D are carbon atoms and one is a nitrogen atom. Preferred among Formula (7) and Formula (8) compounds when a nitrogen is present are those wherein A is nitrogen.

The aromatic ring-fused cyclopentane derivatives of Formula (17) of the current invention are prepared according the methods outlined in Schemes 1 to 3 and in the Examples from compounds of Formula (8) wherein A, B, C and D are carbon atoms or three of A, B, C and D are carbon atoms and one is a nitrogen atom. Preferred among Formula (7) and Formula (8) compounds when a nitrogen is present are those wherein A is nitrogen.

Prepared in synthesizing the indane carboxylates of Formula (18), preferably Compound (g) and Compound (i), are the novel intermediates of Formula (b):

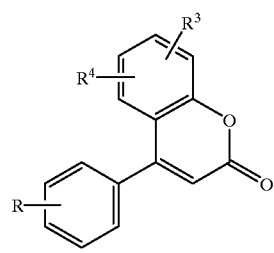

(b)

wherein $R^3$ and $R^4$ are as described in Formula (1) and R is as described in Formula (4).

Also prepared in synthesizing the indane carboxylates of Formula (18), preferably Compound (g) and Compound (i), are the novel intermediates of Formula (c):

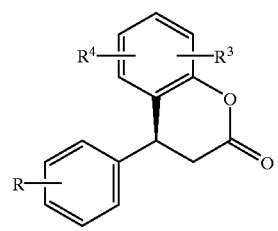

(c)

wherein $R^3$ and $R^4$ are as described in Formula (1) and R is as described in Formula (4).

Also prepared in synthesizing the indane carboxylates of Formula (18), preferably Compound (g) and Compound (i), are the novel intermediates of Formula (d):

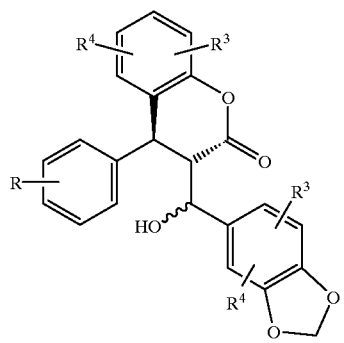

(d)

wherein R³ and R⁴ are as described in Formula (1) and R is as described in Formula (4).

Also prepared in synthesizing the indane carboxylates of Formula (18), preferably Compound (g) and Compound (i), are the novel intermediates of Formula (e):

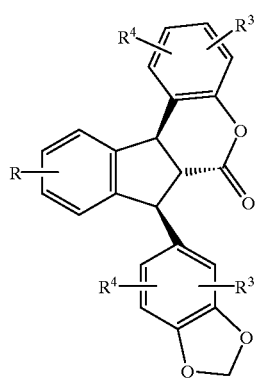

(e)

wherein R³ and R⁴ are as described in Formula (1) and R is as described in Formula (4).

Also prepared in synthesizing the indane carboxylates of Formula (18), preferably Compound (g) and Compound (i), are the novel intermediates of Formula (f):

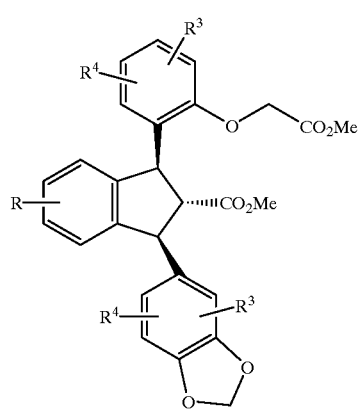

(f)

wherein R³ and R⁴ are as described in Formula (1) and R is as described in Formula (4).

Also prepared in synthesizing the indane carboxylates of Formula (18), preferably Compound (i), are the novel intermediates of Formula (h):

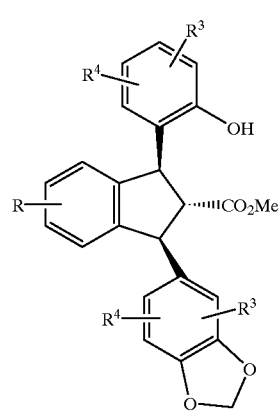

(h)

wherein R³ and R⁴ are as described in Formula (1) and R is as described in Formula (4).

Also prepared in synthesizing the indane carboxylates of Formula (18), preferably Compound (g) and Compound (i), are the novel intermediates of Formula (j):

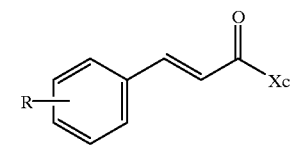

(j)

wherein R is as described in Formula (4).

Also prepared in synthesizing the indane carboxylates of Formula (18), preferably Compound (g) and Compound (i), are the novel intermediates of Formula (1):

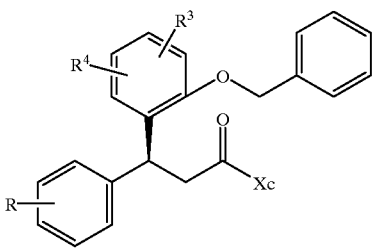

(l)

wherein R³ and R⁴ are as described in Formula (1) and R is as described in Formula (4).

Also prepared in synthesizing the indane carboxylates of Formula (18), preferably Compound (g) and Compound (i), are the novel intermediates of Formula (m):

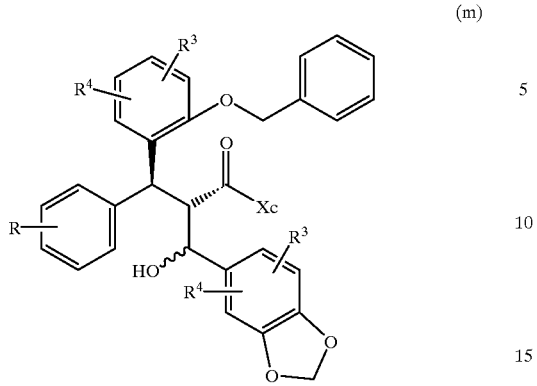

(m)

wherein $R^3$ and $R^4$ are as described in Formula (1) and R is as described in Formula (4).

Prepared in synthesizing the aromatic ring-fused cyclopentane derivatives of Formula (1) are the novel intermediates of Formula (9):

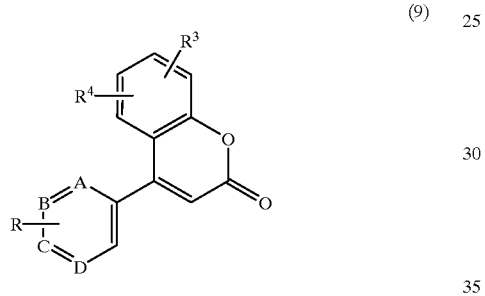

(9)

wherein A, B, C and D are carbon atoms or three of A, B, C and D are carbon atoms and one is a nitrogen atom, $R^3$ and $R^4$ are as described in Formula (1) and R is as described in Formula (4).

Prepared in synthesizing the cyclopenteno[b]pyridine derivatives of Formula (19) are intermediates of Formula (9) where three of A, B, C and D are carbon atoms and one is a nitrogen atom, $R^3$ and $R^4$ are as described in Formula (1) and R is as described in Formula (4).

Also prepared in synthesizing the cyclopenteno[b] pyridine derivatives of Formula (19) are the novel intermediates of Formula (10):

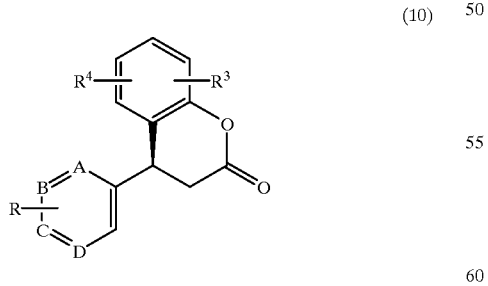

(10)

wherein three of A, B, C and D are carbon atoms and one is a nitrogen atom, $R^3$ and $R^4$ are as described in Formula (1) and R is as described in Formula (4).

Also prepared in synthesizing the cyclopenteno[b] pyridine derivatives of Formula (19) are the novel intermediates of Formula (11):

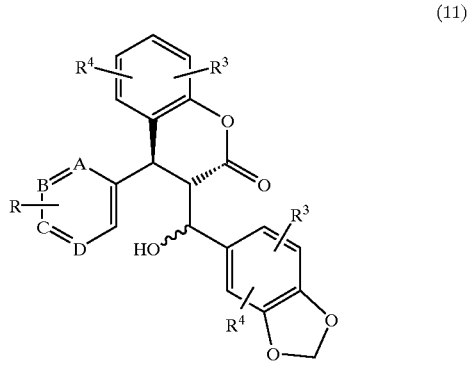

(11)

wherein three of A, B, C and D are carbon and one is nitrogen, $R^3$ and $R^4$ are as described in Formula (1) and R is as described in Formula (4).

Also prepared in synthesizing the cyclopenteno[b] pyridine derivatives of Formula (19) are the novel intermediates of Formula (12):

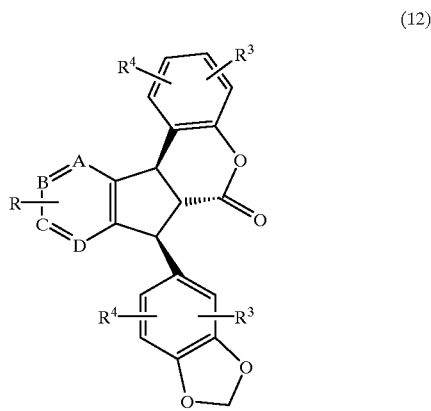

(12)

wherein three of A, B, C and D are carbon and one is nitrogen, $R^3$ and $R^4$ are as described in Formula (1) and R is as described in Formula (4).

Also prepared in synthesizing the cyclopenteno[b] pyridine derivatives of Formula (19) are the novel intermediates of Formula (13):

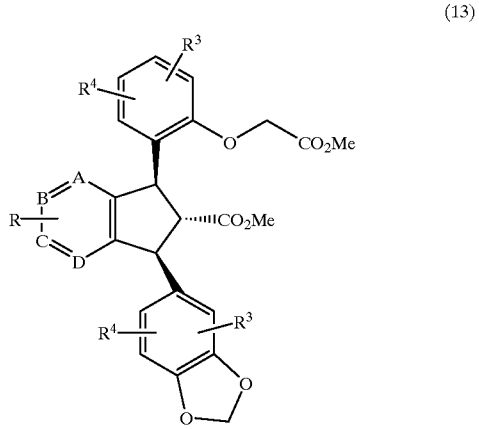

(13)

wherein three of A, B, C and D are carbon and one is nitrogen, $R^3$ and $R^4$ are as described in Formula (1) and R is as described in Formula (4).

Also prepared in synthesizing the cyclopenteno[b]pyridine derivatives of Formula (19) are the novel intermediates of Formula (14):

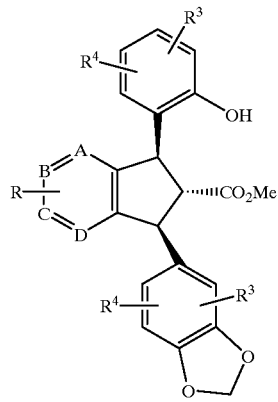
(14)

wherein three of A, B, C and D are carbon and one is nitrogen, $R^3$ and $R^4$ are as described in Formula (1) and R is as described in Formula (4).

Also prepared in synthesizing the cyclopenteno[b]pyridine derivatives of Formula (19) are the novel intermediates of Formula (15):

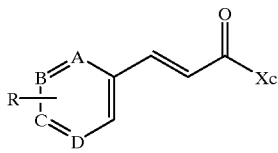
(15)

wherein three of A, B, C and D are carbon atoms and one is a nitrogen atom and R is as described in Formula (4).

Also prepared in synthesizing the cyclopenteno[b]pyridine derivatives of Formula (19) are the novel intermediates of Formula (16):

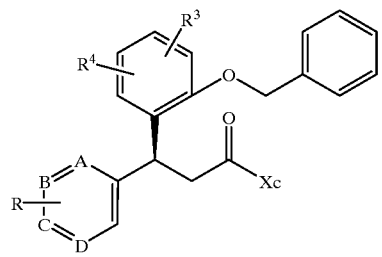
(16)

wherein three of A, B, C and D are carbon atoms and one is a nitrogen atom; $R^3$ and $R^4$ are as described in Formula (1) and R is as described in Formula (4).

Also prepared in synthesizing the cyclopenteno[b]pyridine derivatives of Formula (19) are the novel intermediates of Formula (25):

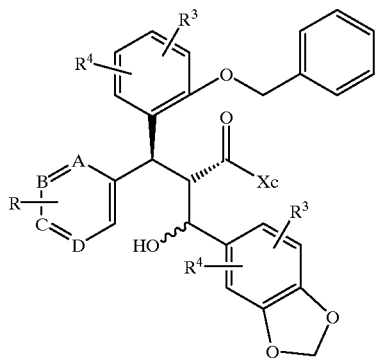
(25)

wherein three of A, B, C and D are carbon atoms and one is a nitrogen atom; $R^3$ and $R^4$ are as described in Formula (1) and R is as described in Formula (4).

Prepared in synthesizing the aromatic ring-fused cyclopentane derivatives of Formula (1) are the novel intermediates of Formula (20):

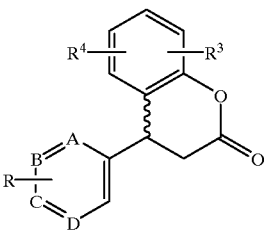
(20)

wherein A, B, C and D are carbon atoms or three of A, B, C and D are carbon atoms and one is nitrogen, $R^3$ and $R^4$ are as described in Formula (1) and R is as described in Formula (4).

Also prepared in synthesizing the aromatic ring-fused cyclopentane derivatives of Formula (1) are the novel racemic intermediates of Formula (21):

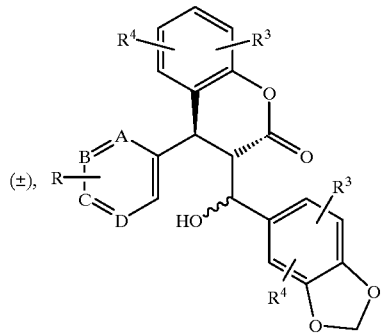
(21)

wherein A, B, C, and D are carbon atoms or three of A, B, and D are carbon atoms and one is a nitrogen atom; $R^3$ and $R^4$ are as described in Formula (1) and R is as described in Formula (4).

Also prepared in synthesizing the aromatic ring-fused cyclopentane derivatives of Formula (1) are the novel racemic intermediates of Formula (22): and R is as described in Formula (22).

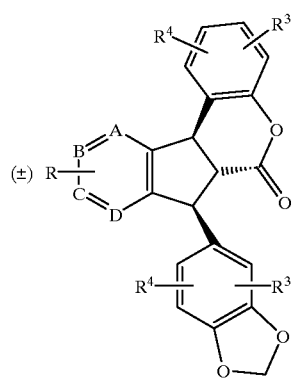

(22)

wherein A, B, C and D are carbon atoms or three of A, B, C and D are carbon atoms and one is a nitrogen atom; $R^3$ and $R^4$ are as described in Formula (1) described in Formula (4).

Also prepared in synthesizing the aromatic ring-fused cyclopentane derivatives of Formula (1) are the novel racemic intermediates of Formula (23):

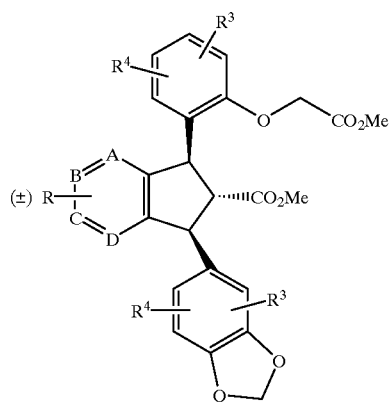

(23)

wherein A, B, C and D are carbon atoms or three of A, B, C and D are carbon atoms and one is a nitrogen atom; $R^3$ and $R^4$ are as described in Formula (1) and R is as described in Formula (4).

Also prepared in synthesizing the aromatic ring-fused cyclopentane derivatives of Formula (1) are the novel racemic intermediates of Formula (24):

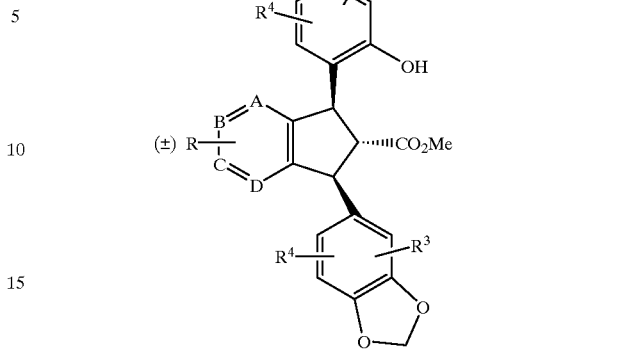

(24)

wherein A, B, C and D are carbon atoms or three of A, B, C and D are carbon atoms and one is a nitrogen atom; $R^3$ and $R^4$ are as described in Formula (1) and R is as described in Formula (4).

All of the starting materials and reagents used herein are known and readily available or can be easily made from known and readily available reagents.

For example, Rh-(S,S)(Chiraphos)(NBD)ClO$_4$. THF and Ru-(S)-(−)-BINAP are obtained from the Aldrich chemical company Milwaukee, Wis.

For example, (E)-3-(3'-propyloxyphenyl)-2-propenoyl chloride, used in Example 3 (i), can be prepared from commercially available 3-hydroxybenzaldehyde by reacting 3-hydroxybenzaldehyde with 1-iodopropane to give 3-propyloxy benzaldehyde. 3-Propyloxy benzaldehyde is then reacted with malonic acid to give the corresponding propenonic acid which is subsequently converted into (E)-3-(3'-propyloxyphenyl)-2-propenoyl chloride by reaction with oxalyl chloride.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

Example 1—Corresponding to Scheme 1

(+) (1S, 2R, 3S)-3-(2-Carboxymethoxy-4-methoxvphenvl)-1-(3,4-methylenedioxyphenyl)-5-(prop-1-yloxy)indane-2-carboxylic acid disodium salt (i). Methlyl 3-hydroxybenzoylacetate (a compound of Formula (a))

THF (10.0 L), 60% NaH (2.00 kg), and dimethyl carbonate (6.50 kg) were charged to a reaction vessel and stirred while heating to 55–60° C. A solution of 3-hydroxyacetophenone (2.70 kg) (a compound of Formula (4)) in THF (10.0 L) was added to the reaction mixture over 75 minutes, maintaining the reaction temperature at 55–60° C. during the addition. After 20 minutes, TLC indicated that the reaction was complete, so it was cooled to 20–25° C. and quenched carefully with 2.9 M hydrochloric acid (20.0 L). The mixture was extracted three times with toluene (3×10.0 L). All three organic layers were combined, washed with once saturated aqueous NaCl (10.0 L), concentrated by vacuum distillation to about 5 L, and cooled to 35–40° C. The top phase (toluene and the mineral oil from the NaH) was removed and discarded, and the bottom layer (3-hydroxybenzoylacetate (a compound of Formula (a)) and toluene, 5.6 kg total) was used as is in the preparation of 4-[3-(hydroxy)phenyl]-7-methoxycoumarin (a compound of Formula (b)). A sample from the product layer was concentrated in vacuo to remove the toluene, after which it gave the following 300 MHz $^1$H NMR (CDCl$_3$): δ 3.75 (s, 3 H), 4.00 (s, 2 H), 6.51 (br s, 1 H), 7.10 (dd, $J_1$=2 Hz, $J_2$=8 Hz, 1 H), 7.32 (t, J=8 Hz, 1 H), 7.45 (m, 2 H).

(ii). 4-[3'-(hydroxy)phenyl]-7-methoxycoumarin (a compound of Formula (b)) The solution of methyl 3-hydroxybenzoylacetate (about 4.0 kg) and toluene (total weight of solution 5.6 kg) from the step above was charged to a reaction vessel along with 3-methoxyphenol (2.55 kg). The mixture was stirred vigorously at 0° C. while 27 M sulfuric acid (5.55 L) was added over 5 minutes. The resulting dark solution was warmed to 25° C. When the reaction began to thicken (40 minutes), methanol (21.8 L) was added. The addition was exothermic. Continued stirring (15 minutes) yielded a smooth, brown slurry which was cooled to 5° C. over 25 minutes, stirred for one hour, then filtered. The filter cake was washed with methanol (5.50 L) and dried under vacuum at 45–50° C. to give 3.70 kg (13.8 mol, 70% yield for two steps) of 4-[3'-(hydroxy)phenyl]-7-methoxycoumarin (a compound of Formula (b)).

300 MHz $^1$H NMR (DMSO-d$_6$): δ 3.86 (s, 3 H), 6.18 (s, 1 H), 6.90 (m, 4 H), 7.07 (d, J=2 Hz, 1 H), 7.32(d,J=9 Hz, 1 H), 7.38(d,J=10 Hz, 1 H).

(iii). 4-[3'-(Prop-1-yloxy)phenyl]-7-methoxycoumarin (a compound of Formula (b))

4-[3'-(hydroxy)phenyl]-7-methoxycoumarin (1.78 kg) and KCO$_3$ (1.65 kg) were suspended in acetonitrile (7.20 L) and N,N-dimethylformamide (1.80 L) and the mechanically stirred mixture was heated to 65° C. When the reaction had reached 65° C., neat n-propylbromide (1.48 kg) was added and the mixture was stirred another 21 hours. The slurry was heated to 88–109° C. and concentrated by distillation. When 6.8–7.0 L of distillate had been removed, the slurry was cooled to 40° C. and diluted with water (14.4 L) and stirred while cooling slowly to 20° C. The slurry was filtered to collect the title compound as a pink, amorphous solid, which was washed with water (2.0 L). The air-dried product was recrystallized from a mixture of hexanes (11.9 L) and isopropanol (6.2 L) at 50° C. Filtration at 22° C. gave a very pale pink, crystalline solid which was washed with hexanes (250 mL) and air-dried. Weight =1.70 kg (5.58 mol, 83%). A second crop of product was isolated from the partially concentrated mother liquors; the light pink, crystalline solid weighed 307 g (0.989 mol, 15%). 300 MHz $^1$H NMR (CDCl$_3$) δ 1.05 (t, J=7 Hz, 3 H), 1.83 (m, J=7 Hz, 2 H), 3.88 (s, 3 H), 3.96 (t, J=7 Hz, 2 H), 6.21 (s, 1 H), 6.79 (dd, $J_1$=2 Hz, $J_2$=9 Hz, 1 H), 6.88 (d, J=2 Hz, 1 H), 6.94 (m, 3 H), 7.40 (t, J=8 Hz, 1 H), 7.42 (d, J=9 H).

(iiia). 4-[3'-(Prop-1-yloxy)phenyl]-7-methoxycoumarin (a Compound formula (b)); (alternative preparation)

A solution of methyl 3-(prop-1-yloxy)benzoylacetate (745 g) (a compound of Formula (a)) in 1,2-dichloroethane was combined under nitrogen with a solution of 3-methoxyphenol (488 g) in 1,2-dichloroethane (2.5 L) and cooled to 0° C. Concentrated H$_2$SO$_4$ (626 mL) was added dropwise and the mixture was stirred vigorously at RT for 90 minutes. Ethyl acetate (3 L) and H$_2$O (3 L) were added and the layers were equilibrated and separated. The aqueous layer was extracted again with ethyl acetate and the combined organic layers were washed with H$_2$O, 5% aqueous NA$_2$CO$_2$CO$_3$, 5% aqueous NaOH, H$_2$O, and brine (2 L each). The organic phase was dried with MgSO$_4$ and concentrated to dryness to yield 841 g (86%) of 4-[3-(prop-1-yloxy)phenyl]-7-methoxycoumarin. The product was recrystallized from ethanol/isopropanol followed by ethyl acetate/isopropanol to give 533 g (63% recovery) of 4-[3'-(prop-1-yloxy)phenyl]-7-methoxycoumarin. 300 MHz $^1$H NMR (CDCl$_3$) δ 1.05 (t, J=7 Hz, 3 H), 1.83 (m, J=7 Hz, 2 H), 3.88 (s, 3 H), 3.96 (t, J=7 Hz, 2 H), 6.21 (s, 1 H), 6.79 (dd, $J_1$=2 Hz, $J_2$=9 Hz, 1 H), 6.88 (d, J=2 Hz, 1 H), 6.94 (m, 3 H), 7.40 (t, J 8 Hz, 1 H), 7.42 (d, J=9 H).

(iv). 4S-4-[3'-(Prop-1-yloxy)phenyl]-7-methoxy-3,4-dihydrocoumarin (a compound of Formula (c)); (preferred preparation)

A clean 1 L autoclave is charged with 4-[3'-(prop-1-yloxy) phenyl]-7-methoxycoumarin (62.0 g; 0.20mol), abs. methanol (565 mL), [Rh(COD)Cl]$_2$ (245 mg; 0.5 mmol; 0.25 mol %), S,S-Chiraphos (427 mg; 1.0 mmol; 0.5 mol %) and 4 N NaOH (100 mL; 0.4 mol; 2 eq). The sealed vessel is purged with 3×200 psi N$_2$ and 3'200 psi H$_2$. The stirred reaction is run at 50° C., 180–300 psi H$_2$ for 18–24 h. Cool and remove from the vessel.

The methanol solution is concentrated in vacuo to near dryness. The residual brown oil is dissolved in H$_2$O (500 mL) and washed with toluene (2×200 mL). The toluene phases are combined and washed with 1 N NaOH (100 mL). The 1 N NaOH phase is combined with the original aqueous phase. This is acidified to pH 1-2 with 6 N HCl and extracted with toluene (3×300 mL). The combined toluene extracts are washed with sat. NaCl soln (400 mL), dried over MgSO$_4$ (50 g), filtered, and concentrated in vacuo to 300–400 mL.

The toluene solution is treated with p-toluenesulfonic acid monohydrate (2.0 g) and heated to 50° C. for 1 h, or until HPLC indicates that lactonization is complete. The solution is cooled, washed with sat. NaCL soln (300 mL), dried over MgSO$_4$ (30 g), filtered, slurried with florisil (10 g) for 15 min, filtered, and concentrated in vacuo to near dryness as a clear oil. Addition of hexanes (300 mL), to the stirred oil results within 15 min in a white filterable solid of 4S-4-[3'-(Prop-1-yloxy)phenyl]-7-methoxy-3,4-dihydrocoumarin (53.1 g; 85% yield). Chiral HPLC indicates 91.5% ee.

300 MHz $^1$H NMR (CDCl$_3$) δ 1.02 (t, J=7 Hz, 3 H), 1.78 (m, J=7 Hz, 2 H), 3.02 (m, 2H), 3.80 (s, 3 H), 3.88 (t, J=7 Hz, 2 H), 4.24 (t, J=7 Hz, 1 H), 6.63 (dd, $J_1$=2 Hz, $J_2$=8 Hz, 1 H), 6.68 (m, 2H), 6.72(brd,J=8 Hz, 1 H), 6.80 (ddd,$J_1$=0.6 Hz, J$_2$8 Hz, 1 H), 6.68 (m, 2 H), 6.72 (br d, J=8 Hz, 1 H), 6.80 (ddd, $J_1$=0.6 Hz, $J_2$=2 Hz, $J_3$=8 Hz, 1 H), 6.89 (d, J=8 Hz, 1 H), 7.24 (t, J=8 Hz, 1 H).

(iva). 4S-4-[3'-(Prop-1-yloxy)phenyl]-7-methoxy-3,4-dihydrocoumarin (a compound of Formula (c)); (alternative preparation) A solution of 4-[3'-(prop-1-yloxy)phenyl]-7-methoxycoumarin (12.41 g) and [(S)-(−)-2,2'-bis (diphenylphosphino)-1,1'-binaphthyl]chloro(p-cymene) ruthenium chloride (520 mg) in MeOH (94 mL) and 4 N NaOH (20 mL) was shaken at 50° C. under an atmosphere of 3–5 psi H$_2$. After 18 h the reaction was cooled to 23° C., purged with N$_2$, and concentrated in vacuo to approximately ¼ the original volume. The remaining solution was partitioned between H$_2$O (100 mL) and toluene (100 mL). The phases were separated, the aqueous phase was washed with toluene (75 mL), and the combined toluene phases were extracted once with 5% aqueous NaOH. The combined aqueous phases were cooled to 5° C., stirred with toluene (75 mL), and the mixture was acidified to pH 1 with precooled 6 N HCl. After separation, the aqueous phase was extracted with toluene (2×75 mL). The toluene phases were combined, washed with brine (100 mL), dried over $MgSO_4$ (15 g), filtered, and concentrated in vacuo to approximately ½ volume. The remaining solution was treated with p-toluenesulfonic acid monohydrate (0.38 g), and stirred at 50° C. for 1 h. The solution was cooled to 23° C., washed with brine (100 mL), dried over $MgSO_4$ (15 g), filtered, and slurried with Florisil for 15 min. Filtration and concentration in vacuo yielded 4S-4-[3'-(prop-1-yloxy)phenyl]-7-methoxy-3,4-dihydrocoumarin (10.6 g, 85%, 84% ee) as a colorless oil which solidified on standing.

(ivb). 4S-4-[3'-(Prop-1-yloxy)phenyl]-7-methoxy-3,4-dihydrocoumarin (a compound of Formula (c)); (alternative preparation)

A solution of 4-[3'-(prop-1-yloxy)phenyl]-7-methoxycoumarin (12.4 g; 40.0 mmol) and [(2S, 3S)-bis(diphenylphosphino)butane](Bicyclo[2.2.1]hepta-2,5-diene)rhodium perchlorate tetrahydrofuran complex (65 mg) in methanol (94 mL) and 4.0 N NaOH (20 mL) was stirred at 50° C. under 400 psi $H_2$. After 18 h. the reaction was cooled to 23° C. and purged with $N_2$. The clear orange-brown solution (which darkens on exposure to air) was concentrated in vacuo to approximately ¼ the original volume. The remaining solution was partitioned between $H_2O$ (100 mL) and toluene (100 mL). The phases were separated, the aqueous phase was washed with toluene (75 mL), and the combined toluene phases were extracted with 5% aqueous NaOH (30 mL). The combined aqueous phases were cooled to 5° C., stirred with toluene (75 mL), and the mixture was acidified to pH 1 with precooled 6 N HCl. After separation, the aqueous phase was extracted with toluene (3×75 mL). The toluene phases were combined, washed with brine (100 mL), dried over $MgSO_4$ (15 g), filtered, and concentrated in vacuo to approximately ½ volume. The remaining solution was treated with p-toluenesulfonic acid monohydrate (0.38 g), and stirred at 50° C. for 1 h. The solution was cooled to 23° C., washed with brine (100 mL), dried over $MgSO_4$ (15 g), filtered, and slurried with florisil (5.0 g) for 15 min. Filtration and concentration in vacuo yielded 4S-4-[3'-(prop-1-yloxy)phenyl]-7-methoxy-3,4-dihydrocoumarin (9.62 g, 77%, 84% ee) as a colorless oil which solidified on standing.

(v). 3S, 4S-3-(1'-Piperonylalcohol)-4-[3'-(prop-1-yloxy)phenyl]-7-methoxy-3,4-dihydrocoumarin (a compound of Formula (d))

A solution of 4S-4-[3'-(prop-1-yloxy)phenyl]-7-methoxy-3,4-dihydrocoumarin (72.0 g, 92% ee), piperonal (35.0 g), and N,N-diisopropylethylamine (44.6 g) in $CH_2Cl_2$ (720 mL) under nitrogen was cooled to −28° C. The solution was treated with neat $TiCl_4$ (27.9 mL) added over approximately 30 minutes while maintaining the temperature at about −25° C. After stirring about 1.5 hours, the reaction was quenched saturated aqueous $NH_4Cl$ (240 mL) and water (480 mL) and warmed to 15° C. The layers were equilibrated and separated. The organic layer was washed with water (720 mL) and brine (720 mL), dried with $MgSO_4$, and concentrated to give a brittle foam (107 g) consisting of a 1:1 mixture of the two alcohol diastereomers of 3S, 4S-3-(1'-Piperonylalcohol)-4-[3'-(prop-1-yloxy)phenyl]-7-methoxy-3,4-dihydrocoumarin. If desired, the dried organic phase may be used directly in the next reaction, without first concentrating to a foam. 300 MHz $^1H$ NMR, diastereomer A (CDCl$_3$) δ 0.99 (t, J=7 Hz, 3 H), 1.74 (m, J=7 Hz, 2 H), 2.62 (br s, 1 H), 3.28 (dd, J$_1$=3 Hz, J$_2$=9 Hz, 1 H), 3.80 (m, 3 H), 3.86 (s, 3 H), 4.55 (d, J=9 Hz, 1 H), 5.98 (s, 2 H), 6.43 (br s, 1 H), 6.48 (br s, 1 H), 6.48 (d, J=7 Hz, 6.70 (m, 4 H), 6.78 (d, J=8 Hz, 1 H), 6.82 (d, J=1 Hz, 1 H), 6.88 (d, J=9 Hz, 1 H), 7.14 (t, J=8 Hz, 1 H).

300 MHz $^1H$ NMR, diastereomer B (CDCl$_3$) δ 1.01 (t, J=7 Hz, 3 H), 1.76 (m, J=7 Hz, 2 H), 2.71 (br s, 1 H), 3.32 (dd, J$_1$=4 Hz, J$_2$=8Hz, 1 H), 3.83 (t, J=7 Hz, 2 H), 3.82 (s, 3 H), 4.44 (d, J=4 Hz, 1 H), 4.70 (br d, J=7 Hz, 1 H), 5.94 (s, 2 H), 6.53 (br s, 1 H), 6.57 (d, J=8 Hz, 1 H), 6.68 (m, 5 H), 6.81 (d, J=Hz, 1 H), 6.98 (d, J=9 Hz, 1 H), 7.16 (t, J=8 Hz, 1 H).

(va). 3S, 4S-3-(1'-Piperonylalcohol)4-[3'-(prop-1-yloxy)phenyl]-7-methoxy-3,4-dihydrocoumarin (a compound of Formula (d)); (alternative preparation) A solution of 4S4-[3-(prop-1-yloxy)phenyl]-7-methoxy-3,4-dihydrocoumarin (51.5 g, 84% ee) in $CH_2Cl_2$ (400 mL) under nitrogen was cooled in a dry ice/acetone bath. The solution was treated with $TiCl_4$ (198 mL of a 1 M solution in $CH_2Cl_2$) added over 25 minutes followed by neat N,N-diisopropylethylamine (27.8 g) added over 5 minutes. Solid piperonal (25.8 g) was added to the reaction all at once and stirred 1.5 hours. The reaction was quenched 1 N HCl (400 mL) and the layers were equilibrated and separated. The aqueous layer was extracted with $CH_1Cl_2$ (200 mL) and the combined organic layers were washed with brine (600 mL), dried with $MgSO_4$, the dried organic phase is concentrated to yield 3S, 4S-3-(1'-piperonylalchohol)-4-[3-(prop-1-yloxy)phenyl]-7-methoxy-3,4-dihydrocoumarin as a 2:1 mixture of alcohol diastereomers.

(vi). 1S, 2R, 3S-1-Piperonyl-2,3-(7'-methoxy-2',3'-dihydrocoumarinyl)-5-(prop-1-yloxy)indane (a compound of Formula (e))

A solution of 3S, 4S-3-(1'-Piperonylalcohol)-4-[3'-(prop-1-yloxy)phenyl]-7-methoxy-3,4-dihydrocoumarin (106 g) in $CH_2Cl_2$ (850 mL) was heated to 39° C. and treated with neat trifluoroacetic acid (425 mL). The reaction was stirred at about 40° C. for 4.67 hours, then cooled to 20° C. and quenched into 500 mL of ice water. The layers were equilibrated and separated. The organic layer was washed twice with water (2×500 mL) followed by half-saturated aqueous $NaHCO_3$ (500 mL) and saturated aqueous NaCl (300 mL). The organic layer was dried with $MgSO_4$ and concentrated to give a yellow solid (132 g) that was suspended (partially dissolved) in $CH_3CN$ (1200 mL) and stirred at reflux for 2 hours. The slurry was cooled to room temperature and filtered to collect the title compound, which was washed with $CH_3CN$ (50 mL) and air-dried. The white, crystalline solid (94% ee) weighed 46.8 g (46% yield for two steps).

300 MHz $^1H$ NMR (CDCl$_4$) δ 1.09 (t, J=7 Hz, 3 H), 1.86 (m, J=7 Hz, 2 H), 2.98 (dd, J$_1$=11 Hz, J$_2$=14 Hz, 1 H), 3.81 (s, 3 H), 3.99 (t, 2 H), 4.40 (m, 2H), 5,93 (dd, J$_1$=4Hz, J$_2$=1 Hz, 2 H), 6.75 (m, 3 H), 6.79 (s, 1 H), 6.82 (dd, J$_1$=8Hz, J$_2$=2 Hz, 1 H), 6.88 (dd, J$_1$=8Hz, J$_2$=2 Hz, 1 H), 6.94 (br d, J=8 Hz, 1 H), 7.32 (br s, 1 H), 7.75 (br d, J=8 Hz, 1 H).

(via). 1S, 2R, 3S-1-Piperonyl-2,3-(7'-methoxy-2',3'-dihydrocoumarinyl)-5-(prop-1-yloxy)indane (a compound of Formula (e)); (alternative preparation) The solution of 3S, 4S-3-(1'-piperonylalcohol)4-[3'-(prop-1-yloxy)phenyl]-7-methoxy-3,4-dihydrocoumarin, from step (va) above before concentration, (800 mL total volume) was cooled in an ice/water bath and maintained under a nitrogen atmosphere. A solution of $SnCl_4$ in $CH_2C_2$ (176 mL of a 1 M solution) was added to the reaction over 35 minutes. The reaction was stirred at 3–5° C. for 1 hour, then quenched with 800 mL of brine. The layers were equilibrated and separated. The aqueous layer was extracted with $CH_2Cl_2$ (200 mL) and the combined organic layers were dried with $MgSO_4$. The dried organic phase was concentrated to give an orange foam (82.2 g) that was dissolved in $CH_3CN$ (82 mL) and allowed to stand over the weekend. The resulting crystals were collected by filtration and washed with $CH_3CN$ (70 mL) to give 1S, 2R, 3S-1-piperonyl-2,3-(7'-methoxy-2',3'-dihydrocoumarinyl)-5-(prop-1-yloxy)indane as a white solid (8.05 g, 97% ee, 11% yield for steps (iii) and (iv)).

$^1$H NMR ($CDCl_3$) of the crude material, δ 7.13 (d, 1 H), 6.69–6.82 (m, 5 H), 6.48–6.56 (m, 2 H), 6.36 (d, 1 H), 5.94 (s, 2 H), 4.98 (d, 1 H), 4.5–4.65 (m, 3 H), 3.7–3.85 (m, 8 H), 3.6 (s, 3 H), 3.33 (t, 1 H), 1.68–1.80 (m, 2 H), 1.0 (t, 3 H) ppm.

(vii). (+) Methyl (1S, 2R, 3S)-3-(2-carbomethoxymethoxy-4-methoxyphenyl)-1-(3,4-methylenedioxyphenyl)-5-(prop-1-yloxy)indane-2-carboxylate (a compound of Formula (f))

1S, 2R, 3S-1-piperonyl-2,3-(7'-methoxy-2',3'-dihydrocoumarinyl)-5-(prop-1-yloxy)indane (90 mg) was dissolved in acetone (3.0 mL) at 25° C. $K_2CO_3$ (139 mg) followed by methanol (0.10 mL) and methylbromoacetate (37 mg) were added and the mixture was stirred 5 hours at 25° C. Additional methanol (0.40 mL) and methylbromoacetate (12 mg) were added during this time. The reaction was stirred an additional 2 hours at 25° C., then diluted with methyl-tert-butyl ether (30 mL) and washed with brine (2×25 mL). The organic phase was dried with $MgSO_4$ and concentrated to give (+) methyl (1S, 2R, 3S)-3-(2-carbomethoxymethoxy-4-methoxyphenyl)-1-(3,4-methylenedioxyphenyl)-5-(prop-1-yloxy)indane-2-carboxylate (100 mg, 90%) as a viscous oil.

(viii). (+) (1S, 2R, 3S)-3-(2-carboxymethoxy-4-methoxyphenyl)-1-(3,4-methylenedioxyphenyl)-5-(prop-1-yloxy)indane-2-carboxylic acid disodium salt (Compound (g))

To a solution of (+) Methyl (1S, 2R, 3S)-3-(2-carbomethoxymethoxy-4-methoxyphenyl)-1-(3,4-methylenedioxyphenyl)-5-(prop-1-yloxy)indane-2-carboxylate (49.2 g) in isopropanol (1000 mL) and water (48 mL) was added a 50% aqueous solution of sodium hydroxide (179.4 g). The mixture was stirred under nitrogen for 16 hours then concentrated to approximately 200 mL. Water (400 mL) was added and the solution was extracted with t-butyl methyl ether (300 mL). The aqueous layer was acidified with dilute HCl and extracted twice with 300 mL portions of TBME. The organic layer was washed 4 times with water (4×200 mL), then concentrated under reduced pressure. Absolute ethanol was added (400 mL) and the solution was further concentrated to approximately 150 mL. The solution was diluted to 800 mL with absolute ethanol and 60 mL of water. The solution was titrated to pH=11–12 with 1.25 N sodium hydroxide solution then after stirring for 15 minutes, concentrated to an oil. Absolute ethanol (250 mL) was added and the solution reconcentrated to a solid which was triturated with hexane, and filtered. The solid was dried to a constant weight to afford (+) (1S, 2R, 3S)-3-(2-carboxymethoxy-4-methoxyphenyl)-1-(3,4-methylenedioxyphenyl)-5-(prop-1-yloxy)indane-2-carboxylic acid disodium salt.

Example 2-Corresponding to Scheme 2

(+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid ethylene diamine salt (2:1)

(i). (+) Methyl-(1S, 2R, 3S)-3-(2-hydroxy-4-methoxyphenyl)-1-(3,4-methylenedioxyphenyl)-5-(prop-1-yloxy)indane-2-carboxylate (a compound of Formula (h))

1S, 2R, 3S-1-Piperonyl-2,3-(7'-methoxy-2',3'-dihydrocoumarinyl)-5-(prop-1-yloxy)indane (20.0 g) (prepared as described in Example 1 (vi)) was suspended in toluene (160 mL) with powdered $K_2CO_3$ (635 mg, 0.1 equiv) and methanol (120 mL) at room temperature. HPLC of a reaction sample taken after 2 hours of stirring showed no starting material remaining. The reaction was quenched with water (100 mL) and concentrated to a total volume of approximately 200 mL. The mixture was treated with 5% aqueous citric acid (20 mL) and extracted 4 times with toluene (2×40 mL then 2×20 mL). The combined organic phases were washed twice with saturated aqueous NaCl (2×40 mL) and dried by filtration through a pad of $MgSO_4$. Weight-based assay of the toluene solution versus a reference standard showed the presence of 21.4 g (100%) of (+) Methyl-(1S, 2R, 3S)-3-(2-hydroxy-4-methoxyphenyl)-1-(3,4-methylenedioxyphenyl)-5-(prop-1-yloxy)indane-2-carboxylate.

(ia). (+) Methyl-(1S, 2R, 3S)-3-(2-hydroxy-4-methoxyphenyl)-1-(3,4-methylenedioxyphenyl)-5-(prop-1-yloxy)indane-2-carboxylate (a compound of Formula (h)); (alternative preparation)

1S, 2R, 3S-1-Piperonyl-2,3-(7'-methoxy-2',3'-dihydrocoumarinyl)-5-(prop-1-yloxy)indane (prepared as described in Example 1 (via)) (7.33 g) was dissolved in acetone (75 mL) at 25° C. $K_2CO_3$ (11.4 g) and methanol (10 mL) were added and the mixture was stirred at 25° C. for 2 hours. The reaction was concentrated to about 80% of its original volume, $H_2O$ (150 mL) was added, and the solution was extracted twice with ethyl acetate. The combined organic phase was washed twice with brine and dried with $MgSO_4$. The solvent was evaporated to give a light brown gum which was dissolved in $CH_2Cl_2$, evaporated to a foam, dissolved in ethyl acetate, and evaporated again to give methyl-(1S, 2R, 3S)-3-(2-hydroxy-4-methoxyphenyl)-1-(3,4-methylenedioxyphenyl)-5-(prop-1-yloxy)indane-2-carboxylate as light reddish-brown foam (7.08 g, 90%).

(ii). (+) (1S, 2R, 3S)-3-[2-(2-Hydroxyeth-1-yloxy)-4-methoxyphenyl]-1-(3,4-methylenedioxyphenyl)-5-(prop-1-yloxy)indane-2-carboxylic acid ethylene diamine salt (2:1) (Compound (i))

To 463.0 g ( 21.7% wt/wt, 203.8 mmol) of a toluene solution of methyl-(1S, 2R, 3S)-3-(2-hydroxy-4-methoxyphenyl)-1-(3,4-methylenedioxyphenyl)-5-(prop-1-yloxy)indane-2-carboxylate was added 425 mL of toluene, 70 g (496 mmol) of potassium carbonate (325 mesh) and 183 g (2.04 mol) of ethylene carbonate. The resulting mixture was heated to approximately 110° C. over a period of 60 minutes then held at this temperature. The progress of the reaction was monitored by HPLC. The reaction was considered complete when less than 1.0% PAR (peak area ratio) of starting material was detected. After approximately 3 hours at or around 110° C., the reaction was cooled to 70° C. and DI water (700 mL) was added. The mixture was stirred for 15 minutes then the aqueous layer was separated. The organic layer was washed with 5% aqueous citric acid solution (500 mL) followed by DI water (500 mL). The organic phase was separated then concentrated under reduced pressure to a viscous oil. The concentrate was diluted with methanol (300 mL) and tetrahydrofuran (500 mL) then a solution of lithium hydroxide monohydrate (28 g, 654 mmol) dissolved in 300 mL of deionized water was added. The resulting solution was heated to reflux (internal temperature 62–65° C.) over approximately 15 minutes and maintained at reflux while monitoring the reaction progress by HPLC. The reaction was considered complete when no intermediates were detected by in-process HPLC analysis.

After approximately 12 hours at reflux the reaction was considered complete and the resulting mixture cooled to ambient temperature. DI water (500 mL) was added and the reaction mixture concentrated under reduced pressure to a volume of approximately 1 L. Toluene (760 mL) followed by citric acid (150 g, 833 mmol) was added to the resulting solution and the mixture stirred for 5 minutes. The bottom aqueous layer was drained and the organic layer was washed twice with aqueous brine solution (600 mL). The organic layer was separated and filtered to afford 868.8 g of (+)(1S, 2R, 3S)]-3-[2-(2-hydroxyeth-1-yloxy)-4-methoxyphenyl]-1-(3,4-methylendioxyphenyl)-5-propoxyindane-2-carboxylic acid as a solution in toluene. HPLC wt/wt assay indicated 11.2% wt/wt (+)(1S,2R,3S)]-3-[2-(2-hydroxyeth-1-yloxy)-4-methoxyphenyl]-1-(3,4-methylendioxyphenyl)-5-(prop-1-yloxy)indane-2-carboxylic acid.

An analytical sample could be obtained by concentration of the toluene in vacuo and recrystallization from 2-propanol. m.p. 125–127° C.

A toluene solution of (+)(1S,2R,3S)]-3-[2-(2-hydroxyeth-1-yloxy)-4-methoxyphenyl]-1-(3,4-methylendioxyphenyl)-5-(prop-1-yloxy)indane-2-carboxylic acid (868.8 g @ 11.2% wt/wt, 192.5 mmol) was concentrated under reduced pressure to a volume of approximately 200 mL. Distillation was discontinued and 2-propanol (500 mL) was added to the concentrate. The organic solution was concentrated again under reduced pressure to a volume of approximately 200 mL. Distillation was discontinued and 2-propanol (500 mL) was added to the concentrate. The resulting solution in 2-propanol was allowed to stir at ambient temperature for approximately 15 minutes to obtain a homogeneous mixture then diluted with an additional 1000 mL of 2-propanol. The resulting solution was heated to approximately 60° C. over a period of 15–20 minutes under a gentle purge of nitrogen. Heating was discontinued and ethylene diamine (11.6 g, 99.5+%, 192.5 mmol) was added. The reaction mixture was cooled to 30–35° C. over a period of 4 hours. As the solution cooled to 57° C., precipitation of the title compound occurred. The resulting slurry was stirred at ambient temperature for approximately 12 hours then cooled to 0° C. an additional 3 hours before isolation of the title compound via filtration. The product was washed with 3 portions of 2-propanol (300 mL) followed by hexanes (600 mL) chilled to 0–5° C. The product was dried in the vacuum oven for approximately 16 hours at 20–25° C. to afford 91.6 g. (87%) of the title compound.

Anal Calcd. for $C_{30}H_{34}NO_8$ C, 67.15; H, 6.39; N, 2.61. Found, C, 67.2; H, 6.48; N, 2.67.

Example 3—Corresponding to Scheme 3

(4S)-4-[3'-Prop-1-vloxy)phenyl]-7-methoxy-3,4-dihydrocoumarin (Compound (c))

(i). (4S)-3-[(E)-3'-(3-propyloxyphenyl)2'-propenoyl]-4-phenyl-2-oxazolidinone

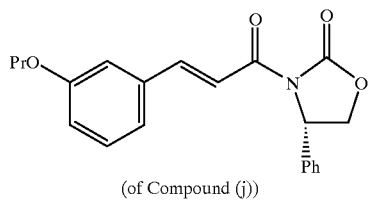

(of Compound (j))

A 500 mL 3-necked flask containing 150 mL of anhydrous THF and 15.9 g (0.098 mol) of (4S)-4-phenyl-2-oxazolidinone was cooled to −73° C. To this solution was added 1.3 equiv. of lithium bis(trimethylsilyl)amide at −73° C. under nitrogen with constant stirring. The solution was stirred at −73° C. for 45 min then allowed to warm to −30° C. when (E)-3-(3'-propyloxyphenyl)-2-propenoyl chloride was added. The solution was stirred at −60° C. for 1 hr then allowed to warm to 0° C. and stirred for 1 hr. The reaction was quenched by pouring into water. The reaction mixture was diluted with 500 mL ethyl acetate and the organic layer was separated. The aqueous layer was washed with ethyl acetate (3×100 mL). The combined organic layer was washed with 2% NaOCl (3×50 mL) then dried over $MgSO_4$ and concentrated to yield a clean yellow oil. This material was recrystallized from EtOAc/hexanes to yield 12.3 g of product: 0.035 mol (46% yield); $^1$H NMR ($CDCl_3$) δ7.8 (q, 2 H); 6.9–7.4 (m, 9 H), 5.5 (dd, 1 H), 4.7 (t, 1 H), 4.3 (dd, 1 H), 3.9 t (2 H), 1.8 (m, 2 H), 1.0 (t, 3 H); $^{13}$C NMR ($CDCl_3$) δ 164.7, 159.4, 153.8, 146.7, 139.0, 135.8, 129.8, 129.2, 128.7, 126.0, 121.2, 117.2, 117.0, 114.0, 70.0, 69.6, 57.9, 22.6, 10.6 ppm.

(ii) (3'S)-(4S)-3-[3'-(3-Propyloxyphenyl)-3'-(4-methoxy-2-benzyloxyphenyl)-1-oxo-propyl]4-phenyl-2-oxazolidinone

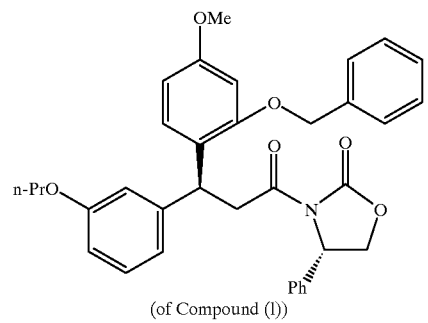

(of Compound (l))

Cuprous bromide-dimethyl sulphide complex (1.648 g, 8 mmol) was added to 21 mL THF and 9 mL of dimethylsulphide in a 3-necked flask at ambient temperature. The suspension was stirred at room temperature 10 min or until solution occurred. The solution was then cooled to −40° C. and the Grignard reagent in THF (16 mmol) prepared from 1-bromo4-methoxy-2-benzyloxybenzene was added at −40° C. The solution was allowed to warm to −10° C. and stirred for 10 min. (4S)-3-[(E)-3'-(3-propyloxyphenyl) 2'-propenoyl]-4-phenyl-2-oxazolidinone (10 mmol) dissolved in 6 mL of dry THF was added over 20 min. The reaction mixture was allowed to stir for 60 min, then was quenched by pouring into aqueous ammonium chloride and extracted with ethyl acetate (3×100 mL). The combined organic layer was dried ($MgSO_4$) then concentrated to yield 5.0 g of crude product.

The crude product was flashed over hexanes/ethyl acetate (7/3, v/v) to yield 3.78 g (0.0067 mol, 67% yield) of a major isomer and 0.71 g (0.00126 mol, 12% yield): for the major isomer, 124–125° C.; $^1$H NMR ($CDCl_3$) δ 7.3–6.4 (m, 17 H), 5.28 (dd, 1 H), 4.9 (m, 3 H), 4.5 (t, 1 H), 4.15 (dd, 1 H), 3.57–3.85 (m, 7 H), 1.77 (m, 2 H), 0.99 (s, 3 H). $^{13}$C NMR ($CDCl_3$) δ 171.1, 159.3, 159.04, 156.76, 153.74, 145.2, 139.0, 139.9, 129.1 (2H), 129.0 (2H), 128.4 (2 H), 127.65, 127.3 (2 H), 125.6, 124.6, 120.3, 114.5, 112.2, 104.4, 100.1, 70.0, 69.9, 69.24, 57.6, 55.3, 40.0, 39.5, 22.6, 10.6 ppm; mass spec (m/z) 565 (M+). Anal. Calcd. for $C_{35}H_{35}NO_6$: C, 74.32; H, 6.24; N, 2.48. Found C, 74.29; H, 6.27; N,2.50.

(iii) (4S)4-[3-Prop-1-yloxy)phenyl]-7-methoxy-3,4-dihydrocoumarin (Compound (c)) (3'S)-(4S)-3-[(E)-3'-(3-propyloxyphenyl)-(4-methoxy-2-benzyloxyphenyl)-1-oxopropyl]-4-phenyl-2-oxazolidinone (0.564 g, 1 mmol) was dissolved in 100 mL of EtOAc and kept under hydrogen pressure (70 psi) with 10% Pd/C as catalyst for 18 hr. The crude reaction mixture was filtered and the ethyl acetate was replaced with toluene and 10% triethylamine. The solution was heated under reflux for 1 hr where TLC indicated the disappearance of starting material. The crude reaction mixture was filtered and flash chromatographed to yield 0.19 g of the desired product (Compound (c)).

Example 4—Corresponding to Scheme 3

3S,4S-3-(1'-Piperonylalcohol)-4-[3-(prop-1-vloxy) phenyl]-7-methoxy-3,4-dihydrocoumarin (Compound (d))

(i). (3'S)-(4S)-3-[2'-Hydroxymethyl(3,4-methylenedioxy) phenyl)-3'-(3-propyloxyphenyl)-3'-(4-methoxy-2-benzyloxyphenyl)-1-oxo-propyl]-4-phenyl-2-oxazolidinone

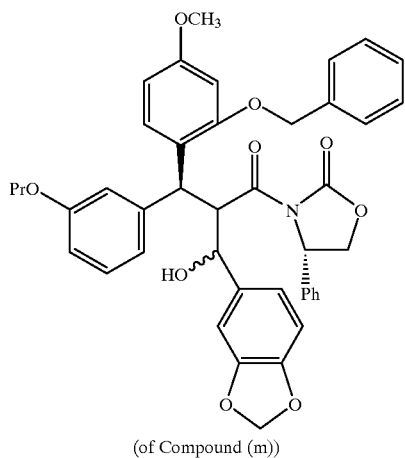

(of Compound (m))

Cuprous bromide-dimethyl sulphide complex (3.5 g, 0.017 mol) was dissolved in 42 mL of THF and 20 mL dimethyl sulphide. The suspension was allowed to stir 10 min until dissolution occurred. The Grignard reagent (0.034 mol) prepared from 1-bromo4-methoxy-2-benzyloxybenzene in THF was added at −40° C. The solution was allowed to warm to −10° C. and stir 10 minutes. (4S)-3-[(E)-3'-(3-propyloxyphenyl)2'-propenoyl]-4-phenyl-2-oxazolidinone (prepared as described in Example 3 (i)) (0.023 mol) in dry THF, was added at −20° C. The reaction mixture was allowed to stir at −20° C. for 30 min then cooled to −40° C. Piperonal (5.1 g, 0.034 mol) in 5 mL THF was added over 20 min and the solution was allowed to stir at room temperature 18 hr. The reaction mixture was quenched by pouring into aqueous ammonium chloride and extracted with ethyl acetate (3×100 mL). The combined organic layer was dried (MgSO$_4$) then concentrated to yield crude isomer oily product. The product was purified by chromatography with silica gel using 7/3 (hexanes/ethyl acetate, v/v) to furnish 2.4 g of each isomer (30% yield). Isomer one: mp 137–139° C.; mass spec (m/z) 716 (M+H)$^+$; $^1$H NMR (CDCl$_3$) δ 7.6 (d, 1 H, J=8.5 Hz) 7.36–6.5 (m, 20 H), 5.9 (m, 2 H), 5.64 (dd, 1 H), 5.14–4.7 (m, 8 H), 3.8 (m, 5 H), 1.76 (m, 2 H), 1.0 (t, 3 H, J=7.4 Hz); $^{13}$C NMR (CDCl$_3$) δ 175.6, 159.7, 158.9, 157.5, 152.8, 147.5, 146.5, 143.4, 138.2, 137.0, 136.9, 129.0 (2), 128.9, 128.5, 128.3, 127.8, 127.5 (2 H), 127.3, 125.7, 124.9 (2), 127.3, 125.7, 124.9 (2), 121.5, 121.1, 118.7, 114.5, 113.5, 108.0, 106.5, 105.0, 100.9, 100.5, 72.1, 70.3, 69.9, 69.6, 69.4, 57.2, 55.3, 50.8, 22.6; 10.6 ppm. Calcd for C$_{43}$H$_{41}$NO$_9$: C, 72.15; H, 5.77; N, 1.96. Found: C, 72.14; H, 5.79; N, 1.91.

Isomer two: mp 163–165° C.; mass spec (m/z) 716 (M+H)$^+$; $^1$H NMR (CDCl$_3$) δ 7.7 (d, 1 H, J=8.5 Hz) 7.34–6.5 (m, 20 H), 5.9 (m, 2 H), 5.5 (dd, 1 H), 5.24–4.6 (m, 5 H), 4.14–3.6 (m, 7 H), 1.77 (m, 2 H), 1.0 (t, 3 H, J=7.4 Hz); $^{13}$C NMR (CDCl$_3$) δ 174.1, 159.4, 159.3, 156.8, 152.7, 146.6, 147.4, 143.0, 137.0, 137.9, 136.6, 129.5, 128.5 (2 H), 128.0 (2 H), 127.5, 127.1 (2 H), 128.7, 128.3, 124.7, 120.5, 118.4, 115.0, 112.6, 107.9, 105.9, 104.5, 100.6, 72.2, 70.1, 69.6, 69.2, 57.1, 55.2, 52.5, 42.08, 22.6, 10.5 ppm. Calcd for C$_{43}$H$_{41}$NO$_9$: C, 72.15; H, 5.77; N, 1.96. Found: C, 71.77; H, 5.75; N, 1.95.

(ii). 3S, 4S-3-(1'-Piperonylalcohol)-4-[3-(prop-1-yloxy) phenyl]-7-methoxy-3,4-dihydrocoumarin (Compound (d)) The starting material, (3'S)-(4S)-3-[2'-hydroxymethyl(3,4-methylenedioxy)phenyl]-3'-(3-propyloxyphenyl)-3'-(4-methoxy-2-benzyloxyphenyl)-1-oxo-propyl]-4-phenyl-2-oxazolidinone (1.3 g, 1.8×10$^{-3}$ mol), was dissolved in 60 mL of ethyl acetate and kept under 10 psi of hydrogen pressure for 18 h with 0.6 g of 10% palladium on carbon. The reaction mixture was filtered then heated under refluxing ethyl acetate for 1 h. The solvent was removed and the crude product was chromatographed to yield 0.52 g of the title compound.

Example 5—Corresponding to Scheme 1

(+) (1S, 2R, 3S)-3-(2-Carboxymethoxy-4-methoxyphenyl)-1-(3,4-methylenedioxyphenyl)-5-(prop-1-yloxy)indane-2-carboxylic acid disodium salt (i). 4-[3'-(benzyloxy)phenyl]-7-methoxycoumarin (a compound of Formula (b))

4-[3'-(hydroxy)phenyl]-7-methoxycoumarin (prepared as in Example 1 (ii)) (268 g) and 95% sodium methoxide (102 g) were dissolved in methanol (3.00 L) and stirred while heating to 45° C. Benzyl bromide (314 g) was added and the reaction was heated to 60° C. A thick precipitate formed in the pink reaction mixture. After 3 hours, the slurry was cooled in an ice-water bath and filtered to collect the product, which was washed with methanol (500 mL) and water (1.0 L), then dried under vacuum (20 inches of Hg) at 70° C. to give 4-[3-(benzyloxy)phenyl]-7-methoxycoumarin (320 g, 89%).

300 MHz $^1$H NMR (CDCl$_3$) δ 3.88 (s, 3 H), 5.12 (s, 2 H), 6.21 (s, 1 H), 6.76 (dd, J$_1$=2Hz, J$_2$=9Hz, 1 H), 6.89 (d, J=2Hz, 1 H), 7.02 (m, 2 H), 7.12 (dd, J$_1$=2 Hz, J$_2$=8 Hz, 1 H), 7.33 (d,J=9 Hz, 1 H) 7.41 (m, 6H).

(ii). 4S4-[3'-(benzyloxy)phenyl]-7-methoxy-3,4-dihydrocoumarin (a compound of Formula (c)) A clean 500 mL autoclave is charged with 4-[3'-(benzyloxy)phenyl]-7-methoxycoumarin (35.8 g; 0.10 mol), abs. methanol (275 mL), (bicyclo[2.2.1]hepta-2,5-diene)[(2S, 3S)-bis (diphenylphosphino)butane]rhodium(I) perchlorate (727 mg; 1.0 mmol; 1 mol %) and 4 N NaOH (50 mL; 0.2 mol; 2 eq). The sealed vessel is purged with 3×400 psi N$_2$ and 3×400 psi H$_2$. The stirred reaction is run at 50° C., 400 psi H$_2$ for 18–24 h, after which it is cooled and removed from the vessel. The methanol solution is concentrated in vacuo to near dryness. The residual brown oil is dissolved in H$_2$O (250 mL) and washed with toluene (2×100 mL). The toluene phases are combined and washed with 1 N NaOH (50 mL). The 1 N NaOH phase is combined with the original aqueous phase. This is acidified to pH 1–2 with 6 N HCl and extracted with toluene (3×200 mL). The combined toluene extracts are washed with sat. NaCl soln (200 mL), dried over MgSO$_4$ (25 g), filtered, and concentrated in vacuo to 150–200 mL. The toluene solution is treated with p-toluenesulfonic acid monohydrate (1.0 g) and heated to 50° C. for 1 h, or until HPLC indicates that lactonization is complete. The solution is cooled, washed with sat. NaCl soln (150 mL), dried over MgSO$_4$ (20 g), filtered, slurried with florisil (5 g) for 15 min, filtered, and concentrated in vacuo to near dryness as a clear oil. Addition of hexanes (100 mL), to the stirred oil results within 15 min the title compound as a white filterable solid (30.3 g; 84% yield). Chiral HPLC indicates 84% ee.

300 MHz $^1$H NMR (CDCl$_3$) δ 2.99–3.08 (overlapping quartets, 2 H), 3.81 (s, 3 H), 4.25 (br t, J=7 Hz, 1H), 5.02 (s, 2 H), 6.62–6.91 (m, 6 H), 7.24–7.42 (m, 6 H).

(iii). 4S-4-[3'-(hydroxy)phenyl]-7-methoxy-3,4-dihydrocoumarin (a compound of Formula (c))

4S-4-[3'-(benzyloxy)phenyl]-7-methoxy-3,4-dihydrocoumarin (7.09 g), 10% Pd/C (Degussa type E101 NE/W, 50% water wet, 1.45 g), and ethyl acetate (225 mL) were charged to a 500 mL flask on a Parr shaker, purged 5 times with 40 psi H$_2$, then shaken for 48 hours at 40° C. under 40 psi H$_2$. The reaction was filtered to remove the catalyst, concentrated, and dried under vacuum to yield 4S4-[3'-(hydroxy)phenyl]-7-methoxy-3,4-dihydrocoumarin as an oil containing some residual ethyl acetate (6.00 g).

300 MHz $^1$H NMR (CDCl$_3$) δ 2.88–3.04 (overlapping quartets, 2 H), 3.75 (s, 3 H), 4.18 (brt, J=7 Hz, 1H), 6.59–6.66 (m, 3 H), 6.74 (dd, J$_1$=8 Hz, J$_2$=2 Hz, 1 H), 6.85–6.90 (m, 2 H), 7.14 (t, J=8 Hz, 1 H).

(iv). 3S, 4S-3-(1'-Piperonylalcohol)-4-[3'-(hydroxy)phenyl]-7-methoxy-3,4-dihydrocoumarin (a compound of Formula (d))

4S-4-[3'-(hydroxy)phenyl]-7-methoxy-3,4-dihydrocoumarin (20.0 g) was dissolved in methylene chloride (360 mL) with heating. The resulting solution was cooled to −73° C. (internal temperature) and treated sequentially with neat TiCl$_4$ (33.8 g), N,N-diisopropylethylamine (24.4 g), and piperonal (11.2 g) in CH$_2$Cl$_2$ (15 mL). Each addition took about 30 minutes, and the temperature was always kept a @≦−72° C. After stirring 30 minutes, the reaction was quenched with saturated aqueous NH$_4$Cl (200 mL) and water (200 mL) and warmed to 0° C. The layers were equilibrated and separated. The aqueous layer was extracted twice with methylene chloride (2×100 mL) and the combined organic phases were washed three times with water (3×300 mL) and with brine (300 mL). The solution was dried with MgSO$_4$ and concentrated to give a brittle foam (31.1 g) consisting of an approximately 5:1 mixture of the two alcohol diastereomers of 3S, 4S-3-(1'-Piperonylalchohol)-4-[3-(hydroxy)phenyl]-7-methoxy-3,4-dihydrocoumarin.

MS (electrospray) m/z 443 (M+Na)$^+$, 403 (M+H-H$_2$O)$^+$.

(v). 1S, 2R, 3S-1-Piperonyl-2,3-(7'-methoxy-2',3'-dihydrocoumarinyl)-5-(hydroxyl)indane (a compound of Formula (e))

A solution of 3S, 4S-3-(1'-Piperonylalcohol)-4-[3'-(hydroxy)phenyl]-7-methoxy-3,4-dihydrocoumarin (31.1 g) in toluene (620 mL) at 87° C. (internal temperature) was treated with 85% H$_3$PO$_4$ (44.4 g). The reaction was stirred at about 80° C. for 9.5 hours, then cooled to 20° C. and poured into a separatory funnel. The residue in the flask was rinsed into the funnel with hot toluene (2×100 mL) and the toluene solution was diluted with 100 mL of ethyl acetate. The solution was washed twice with water (3×250 mL) followed by saturated aqueous NaCl (150 mL). The organic layer was dried with MgSO$_4$ and concentrated almost to dryness. Ethanol (20 mL) was added and the mixture was again concentrated almost to dryness. The resulting slurry was triturated with another 20 mL of ethanol, then filtered to collect the light yellow solid. The flask was rinsed into the funnel with ethanol (20 mL) and the filter cake was air-dried to give 14.3 g (48% for the combined aldol/cyclization) of a 3.5:1 mixture of 1S, 2R, 3S-1-Piperonyl-2,3-(7'-methoxy-2',3'-dihydrocoumarinyl)-5-(hydroxyl)indane and a regioisomeric cyclization product.

300 MHz $^1$H NMR, 1S, 2R, 3S-1-Piperonyl-2,3-(7'-methoxy-2',3'-dihydrocoumarinyl)-5-(hydroxyl)indane (CDCl$_3$) δ 2.99 (dd, J$_1$=15 Hz, J$_2$=11 Hz, 1 H), 3.81 (s, 3 H), 4.40 (overlapping doublets, looks like triplet; higher field J=15 Hz, 1 H; lower field J=11 Hz, 1 H), 4.92 (s, 1 H), 5.94 (d, J=3 Hz, 2 H), 6.70–6.80 (m, 5 H), 6.86–6.90 (m, 2 H), 7.28 (s or fine d overlapping with CHCl$_3$, 1 H), 7.71 (d, J=8 Hz, 1 H).

300 MHz $^1$H NMR, regioisomer (CDCl$_3$) δ 2.99 (dd, J$_1$=15 Hz, J$_2$=11 Hz, 1 H), 3.80 (s, 3 H), 4.37 (d, J=15 Hz, 1 H) 4.53 (d, J=11 Hz, 1 H), 4.57 (s, 1 H), 5.94 (s, 2 H), 6.70 (d, J=2Hz, 1 H), 6.73 (dd, J$_1$=10Hz, J$_2$ =2Hz, 1 H), 6.81 (d, J=8 Hz, 2 H), 6.88 (s, 1 H), 6.98 (d, J=8 Hz, 1 H), 7.29–7.37 (m, 2 H), 7.74 (d, J=9 Hz, 1H).

(vi). 1S, 2R, 3S-1-Piperonyl-2,3-(7'-methoxy-2',3'-dihydrocoumarinyl)-5-(prop-1-yloxy)indane (a compound of Formula (e))

1S, 2R, 3S-1-Piperonyl-2,3-(7'-methoxy-2',3'-dihydrocoumarinyl)-5-(hydroxyl)indane (14.3 g) was dissolved in THF (160 mL) and stirred in a 20° C. water bath. The clear solution was treated sequentially with triphenylphosphine (14.2 g), 1-propanol (3.24 g), and diisopropyl azodicarboxylate (11.4 g). After 1 hour, the reaction was quenched with water (100 mL). The resulting precipitate was collected by filtration, washed with acetonitrile (20 mL), and triturated with 90 mL of acetonitrile to yield 8.1 g (51%) of 1S, 2R, 3S-1-Piperonyl-2,3-(7'-methoxy-2',3'-dihydrocoumarinyl)-5-(prop-1-yloxy)indane. This compound is then utilized as in Example 1 (vii) and forward to yield final product.

(via). 1S, 2R, 3S-1-Piperonyl-2,3-(7'-methoxy-2',3'-dihydrocoumarinyl)-5-(prop-1-yloxy)indane (a compound of Formula (e)); (alternate preparation)

To a solution of 1S, 2R, 3S-1-Piperonyl-2,3-(7'-methoxy-2',3'-dihydrocoumarinyl)-5-(hydroxyl)indane (100 mg) and Pd(DIPHOS)$_2$ (11 mg) in THF (2.0 ML) was added allyl methyl carbonate (88 mg). The mixture was stirred at 50° C. overnight after which HPLC showed 60% 1S, 2R, 3S-1-Piperonyl-2,3-(7'-methoxy-2',3'-dihydrocoumarinyl)-5-(allyloxyl)indane (compared versus an authentic sample prepared by another method).

1S, 2R, 3S-1-Piperonyl-2,3-(7'-methoxy-2',3'-dihydrocoumarinyl)-5-(allyloxyl)indane (100 mg) was suspended in ethyl acetate (5 mL) with 10% Pd/C (Degussa type E101 NE/W, 50% water wet, 20 mg) in a Parr bottle. The mixture was shaken at 50° C. under 20 psi hydrogen for 1.5 hours. HPLC showed complete conversion to 1S, 2R, 3S-1-Piperonyl-2,3-(7'-methoxy-2',3'-dihydrocoumarinyl)-5-(prop-1-yloxy)indane. This compound is then utilized as in Example 1 (vii) and forward to yield final product.

While the preferred embodiments of the invention are illustrated by the above, it is understood that the invention is not limited to the precise instructions herein disclosed and that the right to all modifications coming within the scope of the following claims is reserved.

What is claimed is:

1. A process for the preparation of compounds of the Formula (19):

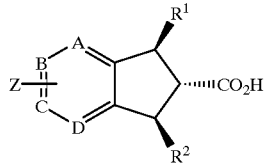
(19)

wherein three of A, B, C and D are carbon atoms and one is a nitrogen atom;

$R^1$ is

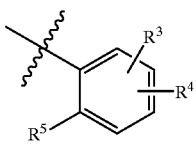

where $R^3$ and $R^4$ are independently H, OH, protected OH, $C_{1-8}$alkoxy, Br, F, I, Cl, $CF_3$ or $C_{1-6}$alkyl and $R^5$ is —$OCH_2CH_2OH$;

$R^2$ is

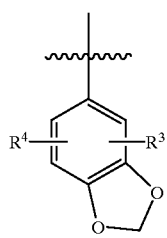

where $R^3$ and $R^4$ are as indicated above and
Z is H, OH, or $C_{1-5}$alkoxy;
or a pharmaceutically acceptable salt thereof, which comprises the steps of (1) treating the compound of Formula (12):

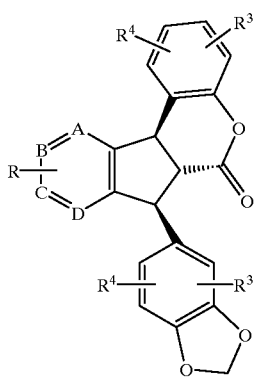
(12)

where A, B, C, D, $R^3$ and $R^4$ are as described above; and

R is H, OH, $C_{1-5}$ alkoxy or a protected oxy group, with potassium carbonate and methanol to form compounds of formula (14):

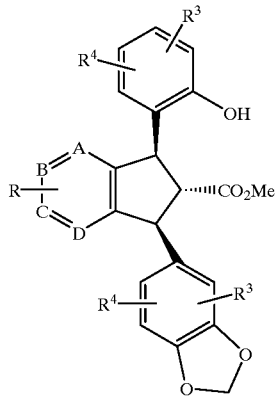
(14)

where A, B, C, D, R, $R^3$ and $R^4$ are as described above;

(2) alkylation of the product of step (1), followed by saponification then treatment with ethylene diamine to form the product of Formula (1) above as the ethylene diamine salt (2:1).

2. A process of claim 1 for the preparation of a compound of Structure (i):

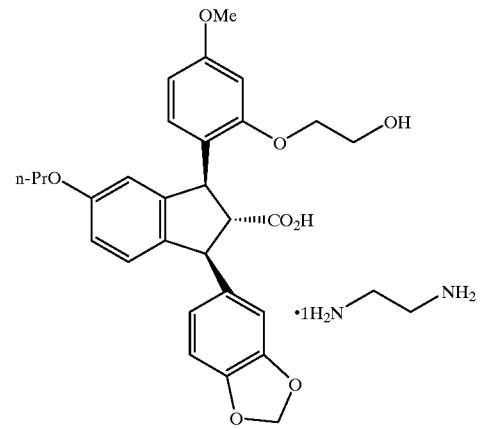
(i)

comprising the steps of:
(1) treating the compound

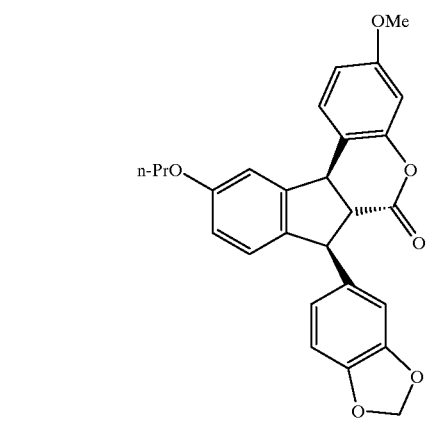

with potassium carbonate and methanol to form the compound (2) alkylation of the product of step (1), followed by saponification to form the compound

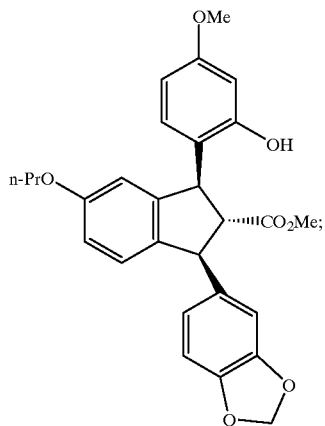

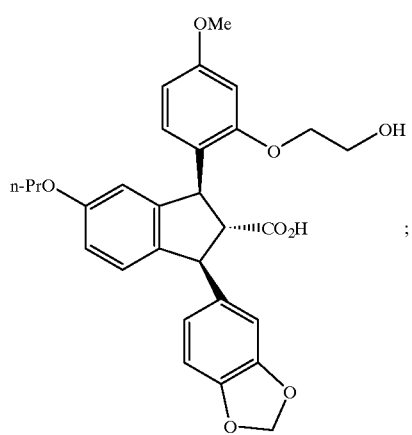
(X)

(3) treating the product of step (2) with ethylene diamine to form the final product, the compound

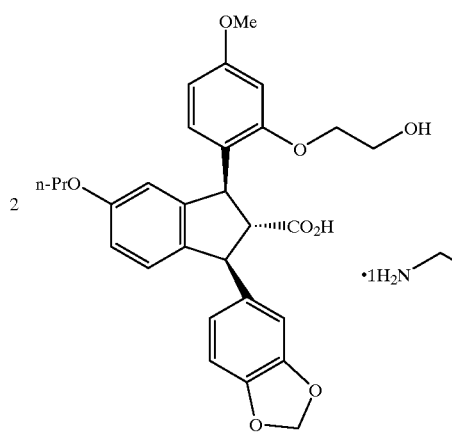
(i)

3. A process for the preparation of a compound of Formula (19), as described in claim 1, or a pharmaceutically acceptable salt thereof, which comprises converting a compound of formula (10),

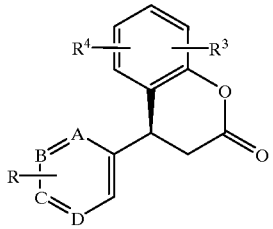
(10)

where A, B, C, D, R, $R^3$ and $R^4$ are as described in claim 1, into a compound of Formula (19), as described in claim 1, and thereafter optionally forming a pharmaceutically acceptable salt thereof.

4. A process for the preparation of a compound of Formula (19), as described in claim 1, or a pharmaceutically acceptable salt thereof, which comprises converting a compound of formula (11),

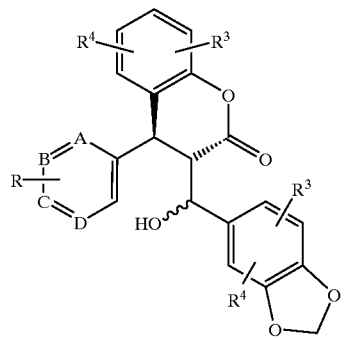
(11)

where A, B, C, D, R, $R^3$ and $R^4$ are as described in claim 1, into a compound of Formula (19), as described in claim 1, and thereafter optionally forming a pharmaceutically acceptable salt thereof.

5. A process for the preparation of a compound of Formula (19), as described in claim 1, or a pharmaceutically acceptable salt thereof, which comprises converting a compound of formula (12),

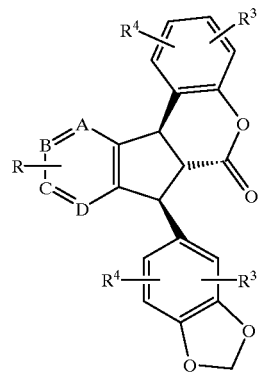
(12)

where A, B, C, D, R, $R^3$ and $R^4$ are as described in claim 1, into a compound of Formula (19), as described in claim 1, and thereafter optionally forming a pharmaceutically acceptable salt thereof.

6. A process for the preparation of a compound of Formula (19), as described in claim 1, or a pharmaceutically acceptable salt thereof, which comprises converting a compound of formula (14),

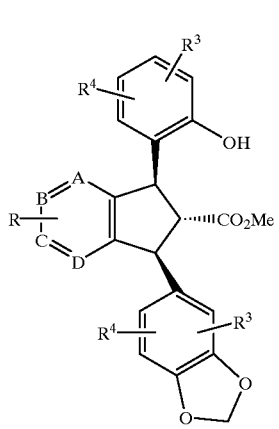
(14)

where A, B, C, D, R, $R^3$ and $R^4$ are as described in claim 1, as described in claim 1, into a compound of Formula (19), as described in claim 1, and thereafter optionally forming a pharmaceutically acceptable salt thereof.

7. A process for the preparation of a compound of Formula (19), as described in claim 1, or a pharmaceutically acceptable salt thereof, which comprises converting a compound of formula (15),

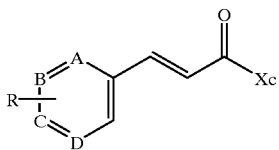
(15)

wherein three of A, B, C and D are carbon atoms and one is a nitrogen atom;

and R is as described in claim 1, into a compound of Formula (19), as described in claim 1, and thereafter optionally forming a pharmaceutically acceptable salt thereof.

8. A process for the preparation of compound X,

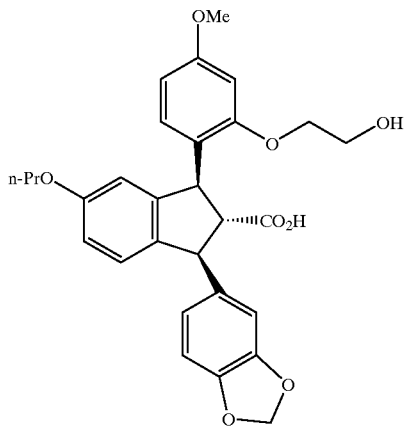
(X)

or a pharmaceutically acceptable salt thereof, which comprises converting the compound

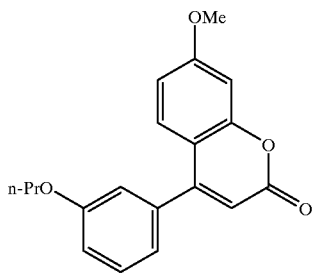

into compound X, and thereafter optionally forming a pharmaceutically acceptable salt thereof.

9. A process for the preparation of compound X,

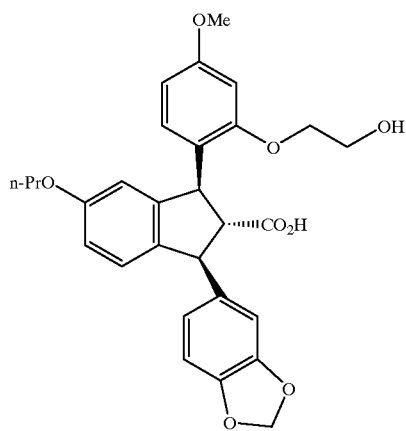
(X)

or a pharmaceutically acceptable salt thereof, which comprises converting the compound

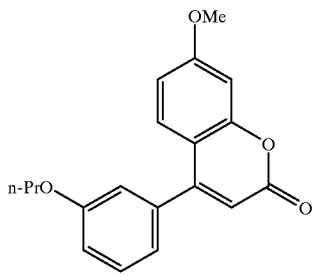

into compound X and thereafter optionally forming a pharmaceutically acceptable salt thereof.

10. A process for the preparation of compound X,

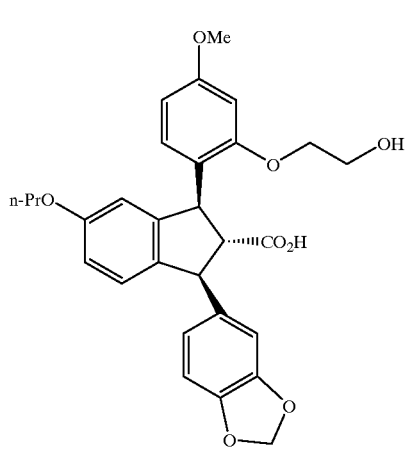

(X)

or a pharmaceutically acceptable salt thereof, which comprises converting the compound

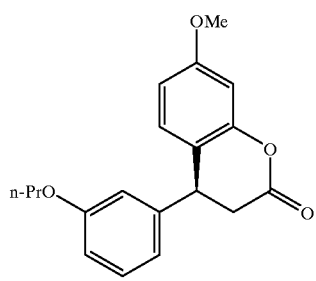

into compound X and thereafter optionally forming a pharmaceutically acceptable salt thereof.

11. A process for the preparation compound X,

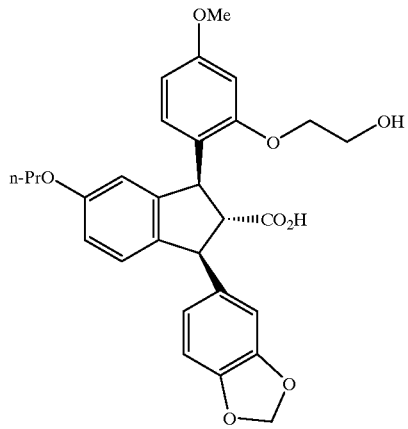

(X)

or a pharmaceutically acceptable salt thereof, which comprises converting the compound

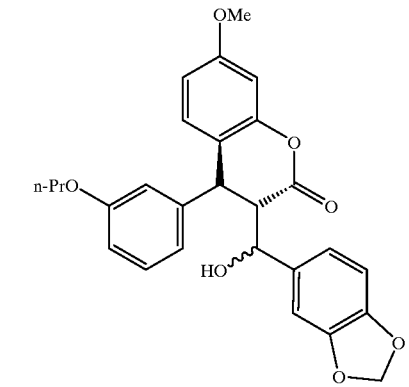

into compound X and thereafter optionally forming a pharmaceutically acceptable salt thereof.

12. A process for the preparation of compound X,

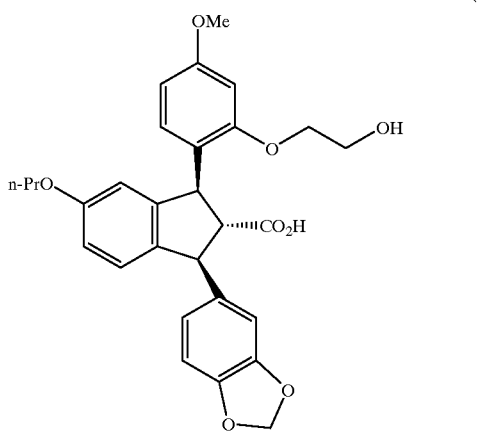

(X)

or a pharmaceutically acceptable salt thereof, which comprises converting the compound

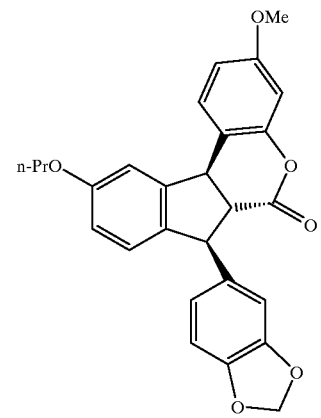

into compound X and thereafter optionally forming a pharmaceutically acceptable salt thereof.

13. A process for the preparation of compound X,

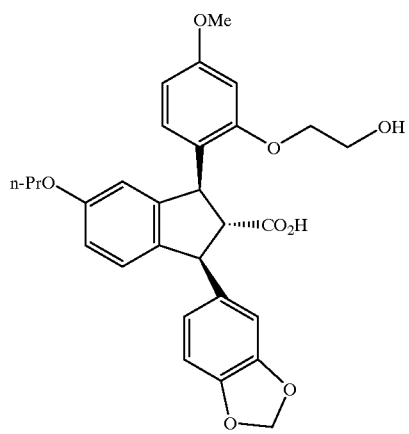
(X)

or a pharmaceutically acceptable salt thereof, which comprises converting the compound

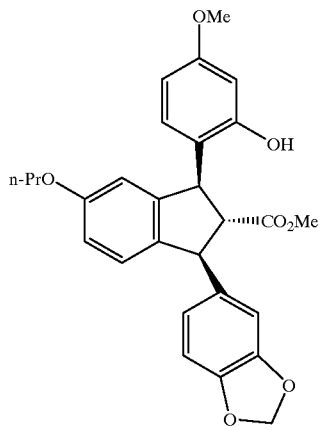

into compound X and thereafter optionally forming a pharmaceutically acceptable salt thereof.

14. A process for the preparation of compound X,

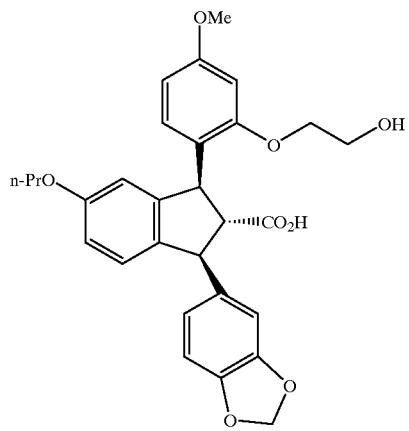
(X)

or a pharmaceutically acceptable salt thereof, which comprises converting the compound

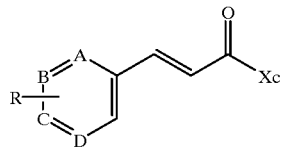
(15)

wherein three of A, B, C and D are carbon atoms and one is a nitrogen atom; and R is as described in claim 1 into compound X and thereafter optionally forming a pharmaceutically acceptable salt thereof.

15. A process for the preparation of compound X,

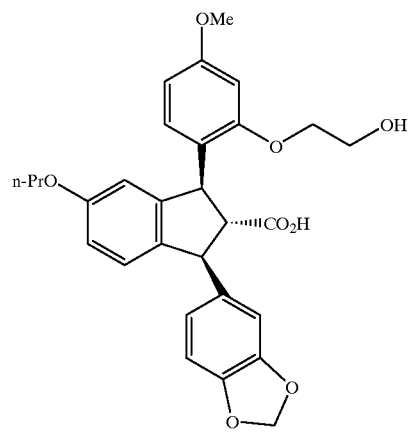
(X)

or a pharmaceutically acceptable salt thereof, which comprises converting a compound of Formula (16):

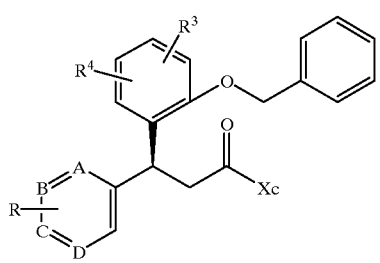
(16)

wherein three of A, B, C and D are carbon atoms and one is a nitrogen atom; and

R, $R^3$ and $R^4$ are as described in claim 1 into compound X and thereafter optionally forming a pharmaceutically acceptable salt thereof.

16. A process for the preparation of compound X,

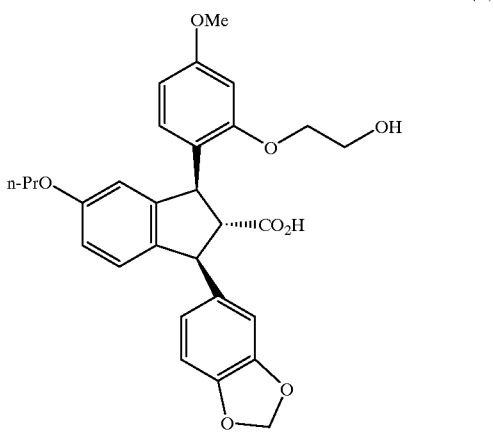

(X)

or a pharmaceutically acceptable salt thereof, which comprises converting a compound of Formula (25):

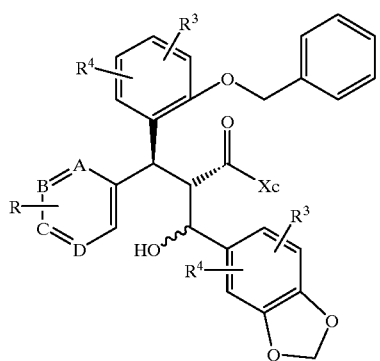

(25)

wherein three of A, B, C and D are carbon atoms and one is a nitrogen atom; and

R, $R^3$ and $R^4$ are as described in claim 1 into compound X and thereafter optionally forming a pharmaceutically acceptable salt thereof.

17. A compound of Formula (19), as described in claim 1, or a pharmaceutically acceptable salt thereof, when prepared by a process which comprises converting a compound of formula (10),

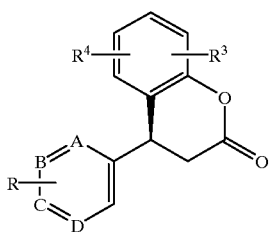

(10)

where A, B, C, D, R, $R^3$ and $R^4$ are as described in claim 1, into a compound of Formula (19), as described in claim 1, and thereafter optionally forming a pharmaceutically acceptable salt thereof.

18. A compound of Formula (19), as described in claim 1, or a pharmaceutically acceptable salt thereof, when prepared by a process which comprises converting a compound of formula (11),

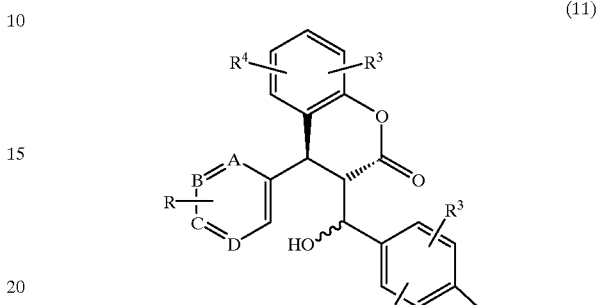

(11)

where A, B, C, D, R, $R^3$ and $R^4$ are as described in claim 1, into a compound of Formula (19), as described in claim 1, and thereafter optionally forming a pharmaceutically acceptable salt thereof.

19. A compound of Formula (19), as described in claim 1, or a pharmaceutically acceptable salt thereof, when prepared by a process which comprises converting a compound of formula (12),

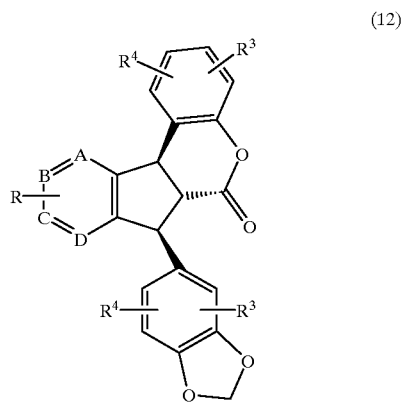

(12)

where A, B, C, D, R, $R^3$ and $R^4$ are as described in claim 1, into a compound of Formula (19), as described in claim 1, and thereafter optionally forming a pharmaceutically acceptable salt thereof.

20. A compound of Formula (19), as described in claim 1, or a pharmaceutically acceptable salt thereof, when prepared by a process which comprises converting a compound of formula (14),

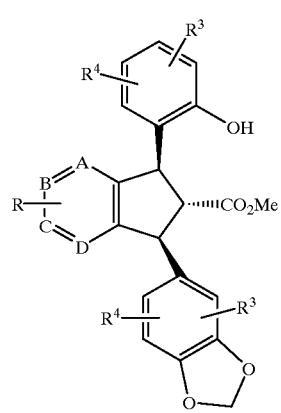

(14)

where A, B, C, D, R, R³ and R⁴ are as described in claim 1, as described in claim 1, into a compound of Formula (19), as described in claim 1, and thereafter optionally forming a pharmaceutically acceptable salt thereof.

21. A compound of Formula (19), as described in claim 1, or a pharmaceutically acceptable salt thereof, when prepared by a process which comprises converting a compound of formula (15),

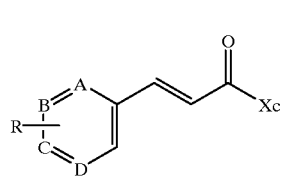

(15)

wherein three of A, B, C and D are carbon atoms and one is a nitrogen atom;

and R is as described in claim 1, into a compound of Formula (19), as described in claim 1, and thereafter optionally forming a pharmaceutically acceptable salt thereof.

22. Compound X,

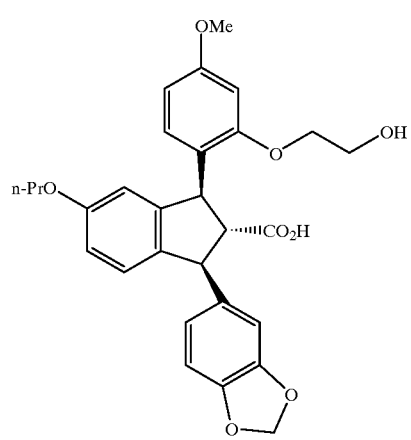

(X)

or a pharmaceutically acceptable salt thereof, when prepared by a process which comprises converting the compound

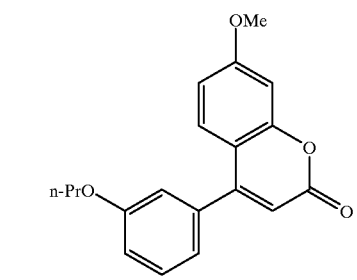

into compound X, and thereafter optionally forming a pharmaceutically acceptable salt thereof.

23. Compound X,

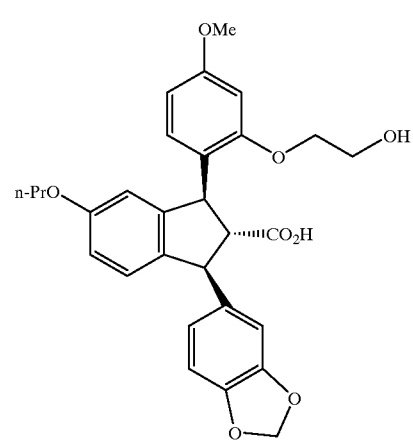

(X)

or a pharmaceutically acceptable salt thereof, when prepared by a process which comprises converting the compound

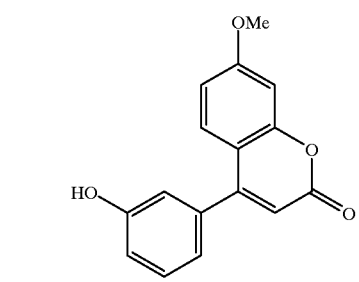

into compound X and thereafter optionally forming a pharmaceutically acceptable salt thereof.

24. Compound X,

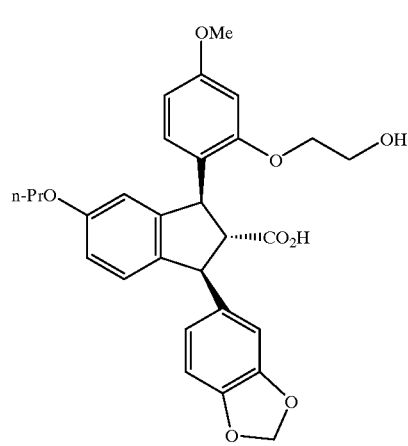

(X)

or a pharmaceutically acceptable salt thereof, when prepared by a process which comprises converting the compound

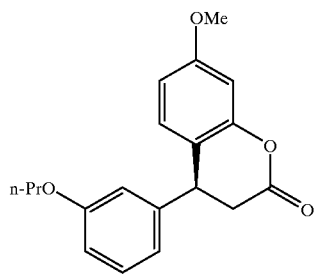

into compound X and thereafter optionally forming a pharmaceutically acceptable salt thereof.

25. Compound X,

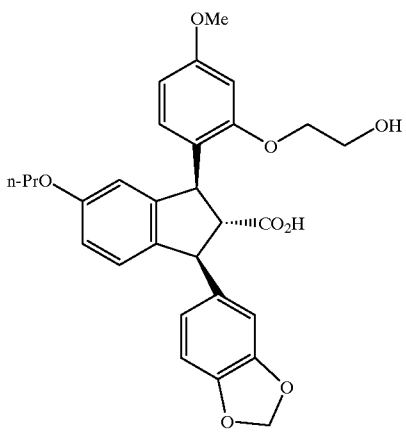

(X)

or a pharmaceutically acceptable salt thereof, when prepared by a process which comprises converting the compound

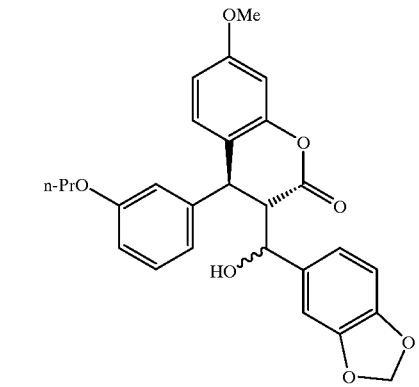

into compound X and thereafter optionally forming a pharmaceutically acceptable salt thereof.

26. Compound X,

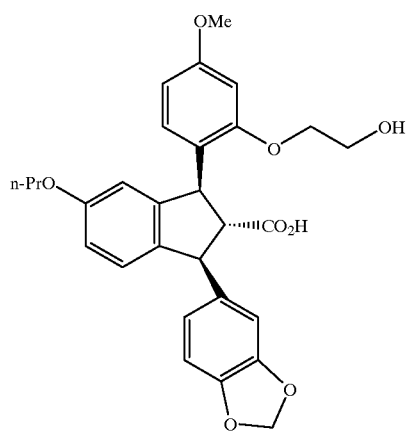

(X)

or a pharmaceutically acceptable salt thereof, when prepared by a process which comprises converting the compound

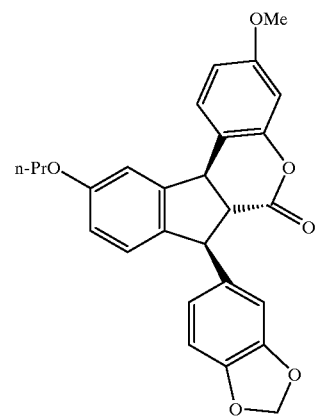

into compound X and thereafter optionally forming a pharmaceutically acceptable salt thereof.

27. Compound X,

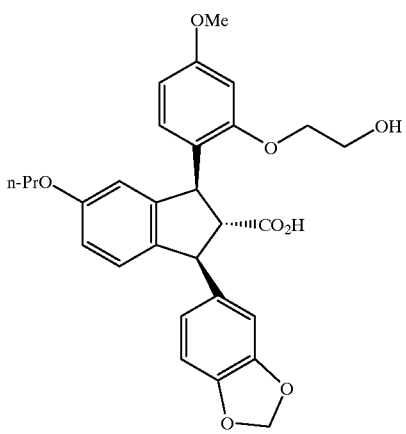
(X)

or a pharmaceutically acceptable salt thereof, when prepared by a process which comprises converting the compound

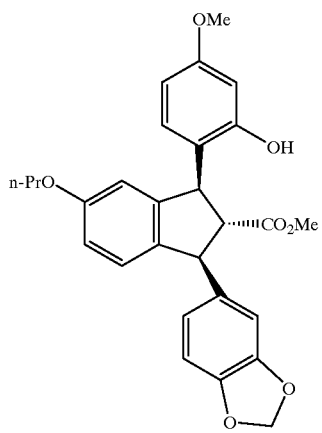

into compound X and thereafter optionally forming a pharmaceutically acceptable salt thereof.

28. Compound X,

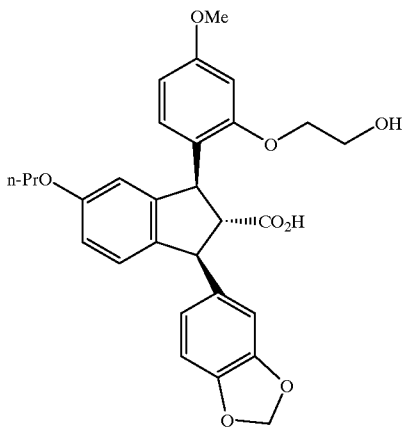
(X)

or a pharmaceutically acceptable salt thereof, when prepared by a process which comprises converting the compound

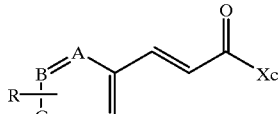
(15)

wherein three of A, B, C and D are carbon atoms and one is a nitrogen atom; and R is as described in claim 1 into compound X and thereafter optionally forming a pharmaceutically acceptable salt thereof.

29. Compound X,

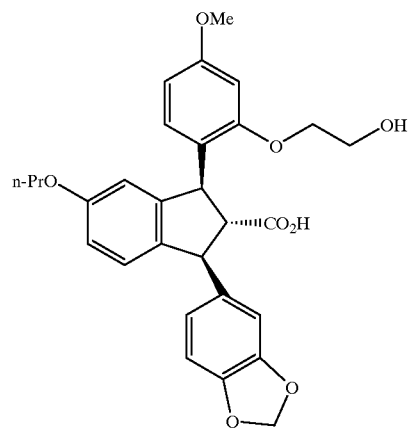
(X)

or a pharmaceutically acceptable salt thereof, when prepared by a process which comprises converting a compound of Formula (16):

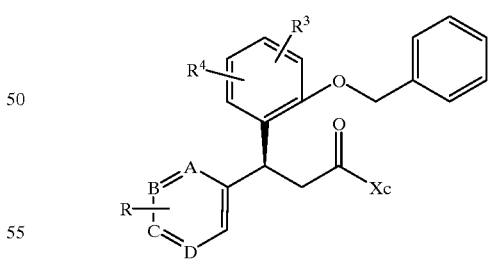
(16)

wherein three of A, B, C and D are carbon atoms and one is a nitrogen atom; and

R, $R^3$ and $R^4$ are as described in claim 1 into compound X and thereafter optionally forming a pharmaceutically acceptable salt thereof.

30. Compound X,
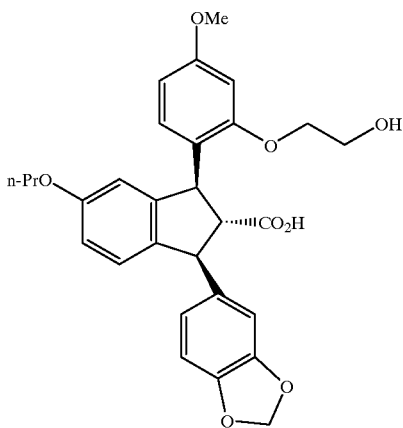
(X)
or a pharmaceutically acceptable salt thereof, when prepared by a process which comprises converting a compound of Formula (25):
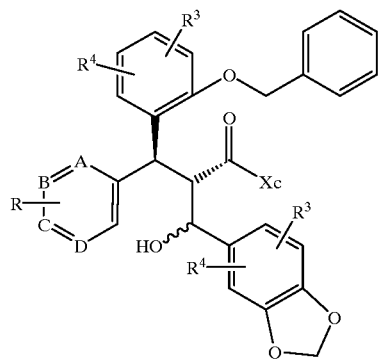
(25)
wherein three of A, B, C and D are carbon atoms and one is a nitrogen atom; and
R, $R^3$ and $R^4$ are as described in claim 1 into compound X and thereafter optionally forming a pharmaceutically acceptable salt thereof.
* * * * *